United States Patent
Dhanoa

(10) Patent No.: US 9,271,980 B2
(45) Date of Patent: *Mar. 1, 2016

(54) DEUTERIUM-ENRICHED PYRIMIDINE COMPOUNDS AND DERIVATIVES

(71) Applicant: Daljit Singh Dhanoa, Del Mar, CA (US)

(72) Inventor: Daljit Singh Dhanoa, Del Mar, CA (US)

( * ) Notice: Subject to any disclaimer, the term of this patent is extended or adjusted under 35 U.S.C. 154(b) by 159 days.

This patent is subject to a terminal disclaimer.

(21) Appl. No.: 13/651,341

(22) Filed: Oct. 12, 2012

(65) Prior Publication Data

US 2013/0040957 A1     Feb. 14, 2013

Related U.S. Application Data

(63) Continuation-in-part of application No. 12/804,970, filed on Aug. 3, 2010, now Pat. No. 8,618,116.

(51) Int. Cl.

| | | |
|---|---|---|
| *A61K 31/519* | (2006.01) | |
| *A61P 25/22* | (2006.01) | |
| *A61P 25/24* | (2006.01) | |
| *A61P 9/12* | (2006.01) | |
| *A61P 35/00* | (2006.01) | |
| *A61P 1/16* | (2006.01) | |
| *A61P 9/10* | (2006.01) | |
| *C07D 495/04* | (2006.01) | |
| *C07D 513/04* | (2006.01) | |
| *C07B 59/00* | (2006.01) | |
| *A61K 45/06* | (2006.01) | |
| *A61K 31/13* | (2006.01) | |
| *A61K 31/445* | (2006.01) | |
| *A61K 31/55* | (2006.01) | |

(52) U.S. Cl.
CPC ............... *A61K 31/519* (2013.01); *A61K 31/13* (2013.01); *A61K 31/445* (2013.01); *A61K 31/55* (2013.01); *A61K 45/06* (2013.01); *C07B 59/002* (2013.01); *C07D 495/04* (2013.01); *C07D 513/04* (2013.01)

(58) Field of Classification Search
CPC ............................. C07D 495/04; A61K 31/519
See application file for complete search history.

(56) References Cited

U.S. PATENT DOCUMENTS

2010/0280050 A1\* 11/2010 Gannon et al. ............ 514/260.1

\* cited by examiner

*Primary Examiner* — Susanna Moore

(57) ABSTRACT

The present invention is concerned with deuterium-enriched pyrimidine compounds of formula I, their derivatives and pharmaceutically acceptable salts and methods of use thereof,

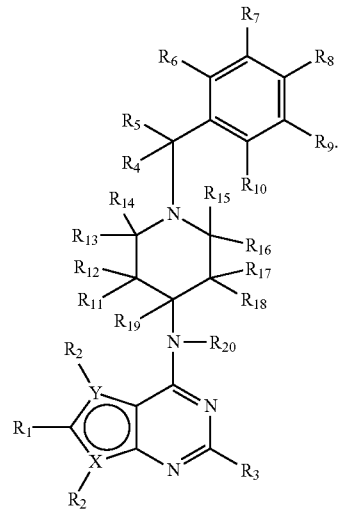

The compounds of formula I are useful for the prevention and treatment of liver fibrosis and cirrhosis, hepatocellular carcinoma, neuroendrcrine neoplasia including metastasis and fibrosis fibrotic processes associated with neuroendocrine cell dysregulation for example Crohn's disease, pulmonary arterial hypertension, pulmonary hypertension associated with chronic obstructive pulmonary disease (COPD), right ventricular hypertrophy, pulmonary vascular remodeling, asthma, cystic fibrosis, hypertension, ischemic stroke, angina pectoris, congestive heart failure, arrhythmia, arterial fibrillation, gastrointestinal disorders, anxiety, depression, stress disorders, post-traumatic stress disorder, obsessive compulsive disorders, demyelinating diseases, acute or chronic cerebrovascular damage, cerebral infarction, subarachanoid hemorrhage, and cerebral edema, neuropathological diseases and cardiovascular system regulation.

19 Claims, No Drawings

DEUTERIUM-ENRICHED PYRIMIDINE COMPOUNDS AND DERIVATIVES

CROSS-REFERENCE TO RELATED APPLICATIONS

This application is a continuation-in-part of U.S. patent application Ser. No. 13/199,940, filed on Sep. 14, 2011, and a continuation-in-part of U.S. patent application Ser. No. 12/804,970, filed on Aug. 3, 2010, each of which is incorporated by reference in its entirety. U.S. patent application Ser. No. 12/804,970 claims the benefit of priority to U.S. Provisional Application No. 61/273,247, filed on Aug. 3, 2009, which is incorporated by reference in its entirety.

FIELD OF THE INVENTION

The invention generally relates to the field of deuterium-enriched pyrimidine compounds, their derivatives, enantiomers, diasteromers, solvates and pharmaceutical salts thereof for the treatment, prevention and potential cure of various diseases including chronic liver diseases, liver cirrhosis, liver fibrosis, hepatocellular carcinoma, liver cancer, renal cell carcinoma, kidney cancer, colorectal cancer, brain cancer, breast cancer, blood cancer, lung cancer, ovarian cancer, pancreas cancer, prostate cancer, stomach cancer, thyroid cancer, testicular cancer, uterus cancer, intestinal cancer, skin cancer, and other forms of cancer, carcinoid tumors, teratocarcinoma, tumor progression, metastasis and fibrosis in the neuroendocrine neoplasia, fibrotic processes associated with neuroendocrine cell dysregulation for example Crohn's disease, chronic kidney disease, Focal Segmental Glomerulosclerosis (FSGS), proteinuria, pulmonary arterial hypertension, pulmonary hypertension associated with chronic obstructive pulmonary disease (COPD), right ventricular hypertrophy, pulmonary vascular remodeling, asthma, cystic fibrosis, hypertension, ischemic stroke, angina pectoris, congestive heart failure, acute myocardial infarction, arrhythmia, arterial fibrillation, neurodenerative diseases, age-related macular degeneration, Alzheimer's disease, dementia, cognition impairment, memory decline, progressive supranuclear palsy, PSP, (a form of frontotemporal demential, FTD), schizophrenia, dementia associated with Parkinson's and Huntington's disease, progressive supranuclear palsy (PSP), Parkinson's disease, psychosis, Huntington disease, Pick's disease and Jacob disease, attention deficit disorder (ADD), attention deficit hyperactivity disorder (ADHD), sleep disorders, insomnia, gastrointestinal disorders including irritable bowel syndrome, gastroesophageal reflux disease, Crohn's disease, gastric emptying disorders, gastritis, emesis, nausea, vomiting, prokinesia, non-ulcer dyspepsia, urinary incontinence, feeding disorders, bulimia, anorexia, obesity, constipation, constipation, and respiratory depression, stress disorders, post-traumatic stress disorder, acute stress disorder, delirium, anxiety, depression, bipolar depression, epilepsy, Down's syndrome, pain, migraine, panic disorders, social phobia, animal phobias, and obsessive compulsive disorders, substance-related disorders including dependence and abuse, intoxication, withdrawal, and delirium arising from the use of alcohol, amphetamines, cannabis, cocaine, hallucinogens, inhalants, nicotine, opioids, hypnotics, and anxiolytics, demyelinating diseases including multiple sclerosis, ALS, peripheral neuropathy, postherpetic neuralgia, cereberal vascular disorders, acute or chronic cereberovascular damage, cerebral infarction, subarachanoid hemorrhage, and cerebral edema, bronchoconstriction, vasodilation, smooth muscle contraction, brain disorders, vascular disorders, blood flow disorders as a result of vasodilation and vasospastic diseases such as angina, vascular headache, Reynaud's disease, pulmonary hypertension, and systemic hypertension; cardiovascular system regulation, prophylaxis and treatment of cerebral infarct, stroke, cerebral ischemia; as well as the treatment of diseases of the intestinal tract, stress-related somatic disorders, bladder function disorders such as cystitis, stress-related urinary incontinence, urinary incontinence post prostate cancer-surgery, reflex sympathetic dystrophy including shoulder/hand syndrome, bladder function disorders such as cystitis, sexual dysfunction, erectile dysfunction, and any nociception, pain or migraine associated with the above mentioned conditions as well as a disease state modulated directly or indirectly with 5-HT receptor, dopamine receptors or multiple kinases.

SUMMARY OF THE INVENTION

This invention is concerned with pyrimidine compounds and their derivatives of the formula I, their non-racemic isomers, enantiomers, diastereomers, mixtures, solvates and pharmaceutical salts thereof,

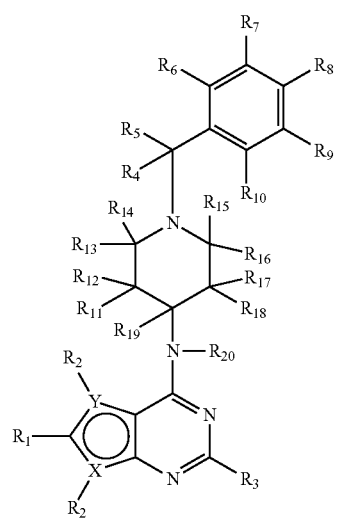

I wherein,
when X=S or O, Y is C or N; when Y is C, it is substituted with $R_2$;
when Y=S or O, X is C or N; when X is C, it is substituted with $R_2$;
$R_1$ is D (Deuterium), F, Cl, $CD_3$, CN, $CF_3$, $CD(CD_3)_2$, i-Bu($d_{1-9}$), $O(CD_2CD_2CD_3)$, Phenyl-$d_5$, 4-F-Ph-$d_4$, deuterated-thiophenyl-$d_3$, deuterated furanyl-$d_3$, deuterated thiazolyl-$d_3$, deuterated-pyridyl ($C_5D_4$), deuterated-imidazolyl-$d_3$, deuterated-pyrrolyl-$d_4$;
$R_2$ is D, F, Cl, $CD_3$, $CF_3$, CN, $OCF_3$, $OCD_3$, $CD(CD_3)_2$, $C_6D_5$, 4-F—$C_6D_4$, 3-F—$C_6D_4$, 2-F—$C_6D_4$; deuterated-thiophenyl-$d_3$, deuterated furanyl-$d_3$, deuterated thiazolyl-$d_3$, deuterated-pyridyl ($C_5D_4$), deuterated-imidazolyl-$d_3$, deuterated-pyrrolyl-$d_4$;
$R_3$ is H, D, $CD_3$, $NHCD_3$, $NHCD_2CD_3$, $NHCD_2CD_2CD_3$, $NHCD_2CD_2CD_2CD_3$, $NHCD_2CD_2CD_2CD_2CD_3$; CN, F, Cl, $OCD_3$, $C_6D_5$, pyridyl-$d_4$;
$R_4$ and $R_5$ independently are D or H, $CD_3$, $CH_3$;
$R_6$, $R_7$, $R_8$, $R_9$ and $R_{10}$ independently are D, H, F, Cl, CN, $CD_3$, $CF_3$, $OCD_3$, $OCF_3$, $OCD_2CD_2CD_3$, $CONDCD_3$, $CON(CD_3)_2$, $SO_2CD_3$, $R_{11}$, $R_{12}$, $R_{13}$, $R_{14}$, $R_{15}$, $R_{16}$, $R_{17}$, $R_{18}$, and $R_{19}$ independently are D, F, H;

$R_{20}$ is D, H;

enantiomers, diastereomers, mixtures and pharmaceutical salts thereof.

The compounds of formula I have antagonist or agonist activity for serotonin (5-HT) receptors, dopamine receptors ($D_1$, $D_2$, $D_3$, $D_4$), sigma receptors, and multiple kinases inhibitor activity.

BACKGROUND OF THE INVENTION

Neurotransmitter serotonin or 5-Hydroxytryptamine (5-HT) is abundantly distributed in the central nervous system, including hippocampus and frontal cortex. 5-HT receptors are a family of G-protein coupled receptors, characterized with 7-transmembrane helices and presently have fourteen known receptor subtypes, some of which exist as multiple splice variants [D. L. Murphy, A. M. Andrews, C. H. Wichems, Q. Li, M. Tohda and B. Greenberg, *J. Clin. Psychiatry*, 1998, 59 (suppl. 15), 4]. 5-HT influences a number of physiological functions and is implicated in a large number of central nervous system disorders, vascular diseases, neurodegenerative diseases and others (Childers, W. E., et. al., *Ann. Rep. Med. Chem.* 2005, 40, 17).

$5-HT_{2B}$ receptors are widely distributed in mammalian peripheral tissues including lung, heart, pancreas, spleen, prostate, liver, vascular and skeletal muscle, adipose tissue, intestine, ovary, uterus, testis, and in the central nervous system (CNS) including brain and cerebral cortex. $5-HT_{2B}$ receptors are expressed in pulmonary endothelial and smooth muscle cells in humans. $5-HT_{2B}$ receptors stimulate calcium release in human endothelial cells from the pulmonary artery (Esteve, J. M., Launay, J. M., Kellerman, O., Maroteaux, L., Functions of serotonin in hypoxic pulmonary vascular remodeling. *Cell Biochem. Biophys*, 2007, 47, 33-44). The receptor was characterized in the rat gastric (fundus) smooth muscle cells initially as the receptor responsible for mediating serotonin-induced contraction in this tissue.

The serotonin receptor $5-HT_{2B}$ regulates cell-cycle progression via receptor tyrosine kinases pathways. It has been reported that activation of the $5-HT_{2B}$ receptor by the neurotransmitter 5-HT leads to cell-cycle progression through retinoblastoma protein hyperphosphorylation and kinases (cyclin D1/cdk$_4$ and cyclin E/cdk$_2$) by induction of cyclin D1 and cyclin E protein. While Cyclin D1 induction is controlled by mitogen-activated protein kinase (MAPK), cyclin E induction is not, indicating an independent regulation of both these cyclins in the $5-HT_{2B}$ receptor mitogenesis. It has also been shown that platelet-derived growth factor receptor (PDGFR) kinase activity is critical for $5-HT_{2B}$-triggered MAPK/cyclin D, but not cyclin E, signaling pathways by using a specific PDGFR inhibitor. Activation of $5-HT_{2B}$ receptor increases activity of the Src kinase family, c-Src, the crucial protein between the Gq-protein coupled receptor $5-HT_{2B}$ and the cell cycle regulators. Inhibition or depletion of c-Src activity eliminates the 5-HT-induced PDGFR tyrosine kinase phosphorylation, MAPK activation, cyclic D1 and cyclin E expression levels and thymidine incorporation (Nebigil, C. G; Launay, J-M; Hickel, P.; Tournois, C.; Maroteaux. et. al. Proc. Natl. Acad. Sci. (PNAS), USA., 2000, 97, 2591-2596).

Ras protein is involved in the signal transduction by the $5-HT_{2B}$ receptor. Activation of the $5-HT_{2B}$ receptor stimulates ras-mitogen activated protein kinase (ERL/MAPK) cascade. The $5-HT_2$ receptors stimulate the phospholipase C second messenger pathway via the α subunit of the Gq GTP-binding protein. Agonist stimulation of the $5-HT_{2B}$ receptor (stably expressed in the mouse fibroblast cell line LMTK) causes rapid and transient activation of the proto-oncogene product p21ras as measured by an increase in GTP-bound Ras in response to 5-HT. Moreover, $5-HT_{2B}$ receptor stimulation activates $p42^{mapk}/p44^{mapk}$ (ERK2/ERK1) mitogen-activated protein kinases as assayed by phosphorylation of myelin basic protein. Furthermore antibodies against p21ras, Gαq, –β, or –γ$_2$ subunits of the GTP-binding protein inhibit MAP kinase-dependent phosphorylation. The MAP kinase activation is correlated with 5-HT-stimulated cell division.

In addition to this mitogenic activity, transforming activity of 5-HT is mediated by the $5-HT_{2B}$ receptor, since its expression in the LMTK cells is absolutely essential for foci formation and subsequently for these foci to form tumors in nude mice. Furthermore, expression of $5-HT_{2B}$ receptors in spontaneous human and *Mastomys natalensis* carcinoid tumors has been detected. Similar to the $5-HT_{2B}$ receptor transfected cells, the *Mastomys* tumor cells are also responsive to 5-HT with similar coupling to p21ras activation. In $5-HT_{2B}$ receptor mitogenesis, c-Src acts alone to control cyclin E induction and in concert with the receptor tyrosine kinase PDGFR to induce cyclin D1 expression via the MAPK/ERK pathway.

Sorafenib (BAY 43-9006, Nexavar), a dual acting multiple kinase inhibitor of RAF/MEK/ERK pathway in tumor cells and tyrosine kinases VEGFR/PDGFR in tumor vasculature has also shown unexpected binding affinity for three 5-HT receptor subtypes including $5-HT_{2B}$ (Ki=56 nM), $5-HT_{2C}$ (Ki=417 nM) and $5-HT_{2A}$ (Ki=1959 nM), with highest binding affinity for the $5-HT_{2B}$ receptor. Sorafenibnib has been approved as an anticancer drug as Nexavar by the USFDA for the treatment of renal cell carcinoma (primary kidney cancer) and hepatocellular carcinoma (advanced primary liver cancer). Regorafenib (BAY-73-4506), a fluoro analog of sorafenib, also a multi-kinase (VEGFR, PDGFR, FGFR, KIT, RET, and Raf), inhibitor for the treatment of various cancers including metastatic colorectal cancer.

$5-HT_{2B}$ receptor antagonists are potential therapeutic agents in the treatment, prevention or cure of certain, multiple or all forms of cancers including kidney, liver, colorectal, breast, colon, thyroid, prostate, blood, head, neck, multiple myeloma, solid tumors and others.

$5-HT_{2B}$ receptor is also a novel target for drug development for the treatment, prevention and cure of chronic liver diseases including liver cirrhosis and fibrosis. It has been shown that $5-HT_{2B}$ receptor antagonist stimulates regeneration of healthy tissue and block fibrosis in chronic liver disease. Furthermore, a $5-HT_{2B}$ antagonist attenuated fibrogenesis and improved liver function in disease models of pre-established and progressive fibrosis (Ebrahimkhani, et. al., Nature Medicine 2011, 17, 1668-1673).

Tissue homeostasis requires effective wound-healing response to injury. In chronic disease, failure to regenerate parenchymal tissue can lead to the replacement of lost cellular mass with a fibrotic matrix. The mechanisms that control the balance of cell regeneration and fibrogenesis are not well established. It has been shown that fibrogenic hepatic stellate cells (HSCs) in the liver are negative regulators of hepatocyte regeneration which requires stimulation of $5-HT_{2B}$ receptors on HSCs by serotonin. Agonism of $5-HT_{2B}$ receptors activates expression of transforming growth factor β1 (TGF-β1) via signaling by mitogen-activated protein kinase 1 (ERK) and the transcription factor JunD. TGF-β1 is a potent suppressor of hepatocyte proliferation. Selective antagonism of $5-HT_{2B}$ receptors enhanced hepatocyte growth in models of acute and chronic liver injury. Similar effects have been observed in $5-HT_{2B}$ knockout mice or JunD knockout mice or upon selective depletion of HSCs in wild-type mice. Antagonism of 5-HT$_{2B}$ attenuated fibrogenesis and improved liver function in disease models in which fibrosis was pre-established and progressive. Thus pharmacological modulation of 5-HT$_{2B}$ receptor may be a safe and effective therapeutic intervention in the treatment, prevention and possibly a cure of chronic liver diseases including but not limited to liver cirrhosis and fibrosis.

Congenital heart failure, pulmonary arterial hypertension and myocardial infarction are major causes of disability and morbidity. The molecular mechanism of cardiac adaptation (hypertrophy) and maladaptation (apoptosis) underlying cardiac pathogenesis is not well understood to date. Several lines of evidence suggest that serotonin (5-hydroxytryptamine, 5-HT) is a neurotransmitter that regulates cardiovascular functions. It has been shown that inactivation of the Gq-coupled 5-HT$_{2B}$R gene leads to partial embryonic lethality due to trabeculae defects. It has been demonstrated that newborn 5-HT$_{2B}$ receptor mutant mice exhibit cardiac dilation resulting from contractility deficits and structural deficits at the intercellular junctions between cardiomyocytes. Cultured cardiomyocytes and 5-HT$_{2B}$ receptor knockout mice were used as an animal model of dilated cardiomyopathy to identify the molecular mechanism of cardiac functions triggered by serotonin (Nebigil, C Etienne, N.; Messaddeq, N.; Maroteaux, L. Serotonin is a novel survival factor of cardiomyocytes: mitochondria as a target of 5-HT$_{2B}$ receptor signaling, *FASEB*, 2003, 17, 1373-1375). These results identify 5-HT as a novel survival factor targeting mitochondria in cardiomyocytes. These findings suggest that the modulation of 5-HT$_{2B}$ receptor signaling have potential application in the prevention and treatment of acute myocardial infarction and congestive heart failure.

Serotonin (5-HT) affects the pulmonary vasculature associated with pulmonary arterial hypertension (PAH) by vasoconstriction, platelet aggregation, and pulmonary arterial smooth muscle cell proliferation. Serotonin receptors subtypes, 5-HT$_{1B}$, 5-HT$_{2A}$ and 5-HT$_{1B}$ have shown evidence for playing a role in the pathology of PAH. 5-HT$_{2B}$ receptors are expressed in pulmonary endothelial and smooth muscle cells and stimulate calcium release in human endothelial cells from the pulmonary artery. It has been demonstrated that 5-HT$_{2B}$ receptors are involved in the development of PH by mediating chronic hypoxic responses in wild-type mice compared with the complete lack of PH and vascular remodeling in the 5-HT$_{2B}$ receptor (−/−) knockout mice in the chronic hypoxic mouse model of PH (Launey et. al., Function of the serotonin 5-Hydroxytryptamine 2B receptor in pulmonary hypertension. *Nat. Med.* 2002, 8, 1129-1135).

5-HT$_{2B}$ receptor modulators (antagonists, partial agonists, inverse agonists and agonists) have the potential to be selective for diseased pulmonary trachea, thymus, thyroid, salivary gland vasculature (i.e., vessels affected by hypoxic conditions) compared to normal pulmonary and systemic vessels. Due to this selectivity, 5-HT$_{2B}$ modulators particularly 5-HT$_{2B}$ antagonists offer a possible therapeutic advantage over the available agents for the treatment of pulmonary arterial hypertension, pulmonary hypertension associated with chronic obstructive pulmonary disease (COPD), right ventricular hypertrophy and related disease of the lung and vascular system.

Pulmonary hypertension (PH) is a progressive, debilitating and often fatal disease that results from an increase in pulmonary blood pressure associated with abnormal vascular proliferation. PH is estimated to affect 100,000 people worldwide. Pulmonary arterial hypertension (PAH) is an increase in the pulmonary vascular resistance due to vasoconstriction and pulmonary vascular remodeling that result in elevated pulmonary arterial pressure. The cause of idiopathic PAH is unknown. PAH can be developed as a consequence of existing diseases such as chronic obstructive pulmonary disease (COPD) hypoxia, portal hypertension, or HIV infection. PAH is progressive and fatal. The median survival time without treatment in adult PAH patients is 2.8 years after diagnosis, and is only 10 months in children. Although survival rates have improved with new drugs, the prognosis is still poor and development of safer and more effective drugs is needed. Current treatments include systemically administered intravenous and subcutaneous prostacyclin analogs and orally active endothelin receptor antagonists, which mainly cause pulmonary arterial dilation to relieve symptoms. There is only one approved orally active agent for PH available for patients, a non-selective endothelin A and B receptor antagonist which requires liver toxicity monitoring.

The role of 5-HT$_{2B}$ in pulmonary hypertension was recognized by the observation that there may be a relationship between the PAH patients taking weight reducing agents such as dexfenfluramine, fenfluramine and aminorex which are 5-HT$_{2B}$ agonists; that the use of these agents may be contributing towards the elevation of pulmonary arterial hypertension (Kramer. M. S., and Lane, D. A. A minorex, dexfenfluramine, and primary pulmonary hypertension, *J. Clin. Epidemiol.* 1998, 51, 361-364). Both a minorex and fenfluramine elevates 5-HT levels by increasing the release of 5-HT from platelets and inhibiting the metabolism and the reuptake of 5-HT (Maclean, M. R., Pulmonary hypertension, anorexigens, and 5-HT: pharmacological synergism in action? *Trends Pharmacology. Sci.* 1999, 20, 490-495; Belohlavkova, S., Simok, J., Kokesova, A., Hnilickova, O., Hampl, V., Fenfluramine-induced pulmonary vasoconstriction: role of serotonin receptors and potassium channels. J. Appl. Physiol. 2001, 91, 755-761). Dexfenfluramine has binding affinity for 5-HT$_2$ receptors and its major metabolite, N-de-ethylated dexfenfluramine is a potent agonist of the 5-HT$_{2B}$ receptor and thus is involved in the development of PAH.

A novel and potent 5-HT$_{2B}$ receptor antagonist has been shown to significantly reduce the elevation in pulmonary arterial pressure and right ventricular hypertrophy and also maintains cardiac function. Pulmonary vascular remodeling was also decreased in rats. A 5-HT$_{2B}$ antagonist was shown to prevent the severity of PAH in the rat model (Porvasnik, S. L., Germain, S., Embury, J., Ganon, K. S., Jacques, V., Murray, J., Byrne, B. J., Shacham, S., Al-Mousily, F., *J. Pharmaco. Exp. Ther.* 2010, 334, 364-372).

The 5-HT$_{2B}$ receptor has also been shown to play a key role in the regulation of neuroendocrine tumor cell proliferation and the modulation of the fibroblast component of the neoplastic microenvironment (Svejda, B., et. al. *Cancer* 2010, 116, 2902-12). Small intestinal neuroendocrine tumors (SI-NETs) are cancers originating from serotonin-producing enterochromaffin cells in the diffuse neuroendocrine system. The carcinoid syndrome reflects excessive serotonin release. Carcinoid syndrome symptomatology includes bronchoconstriction, flushing, diarrhea, and fibrosis in the local peritumoral tissue and at distant in the heart or lungs. 5-HT shows both mitogenic and fibrogenic effects in fibroblasts, smooth muscle cells, and endothelial cells. These effects are mediated via the G-protein coupled 5-HT receptors, which activate mitogenic pathways through the extracellular signal-regulated kinase (ERK) pathway and JNK activation. Other studies have reported that 5-HT modulates valvular subendocardial cell proliferation. The human heart valves express messenger ribonucleic acid (mRNA) for 5-HT agonists (fenfluramine, dexfenfluramine, pergolide, cabergoline, ergotamine) are associated with pulmonary fibrosis and valvular heart disease (Roth, B., Drugs and valvular heart disease. *N. Engl. J. Med.* 2007, 356, 6-9; Gustafsson, B, Hauso, O., Drozdov, I., Kidd, M., Modlin, I., Cacinoid heart disease. *Int. J. Cardio.* 2008, 129, 318-324). Significant evidence exists for involvement of 5-HT$_{2B}$ receptors in cellular pathways that culminate in fibrosis. It has been recognized that SI-NETs are often present with fibrosis in the peritumoral tissue, the adjacent mesentery and peritoneum as well as in the right side of the heart or lungs (Modlin, I., Moss, S., Chung, D., Jensen, R., Snyderwine, E., Priorities for improving the management of gastroentero-pancreatic neuroendocrine tumors. *J. Natl. Cancer. Inst.* 2008, 100, 1282).

The proliferative activity of 5-HT has been shown to be dependent on the expression of 5-HT$_2$ receptor subtypes (Kidd, M., et. al. Inhibition of proliferation of small intestinal and bronchopulmonary neuroendocrine cell lines by using peptide analogs targeting receptors. *Cancer.* 2008, 112, 1404-1414). Similar proliferation effects have been observed in the 5-HT secreting prostate cancer cell line PC3 (Dizeyi, N., et. al. Expression of serotonin receptors 2B and 4 in human prostate cancer tissue and effects of their antagonists on prostate cancer cell lines. *Eur. Urol.* 2005, 47, 895-900), 5-HT$_{2A}$ receptor expressing breast cancer cell line MCF-7 (Sonier, B., et. al. The 5-HT$_{2A}$ serotoninergic receptor is expressed in the MCF-7 human breast cancer cell line and reveals a mitogenic effect of serotonin. Biochem. Biophys. Res. Commun. 2006, 343, 1053-1059), and in human choricarcinoma cell line JEG-3 and BeWO (Sonier, B., et. al. Expression of the 5-HT$_{2A}$ serotoninergic receptor in human placenta and choriocarcinoma cells: mitogenic implications of serotonin. *Placenta.* 2005, 26, 484-490).

During the investigation of signal transduction pathways involved in the antiproliferative effect of 5-HT$_{2B}$ receptor antagonist, by investigating phosphorylation of ERK, direct role of 5-HT$_2$ receptor subtypes has been demonstrated in vascular and tracheal smooth muscle cell proliferation. The mechanism involves coupling of 5-HT$_{2A}$ receptors and the ERK pathway, while 5-HT$_{2B}$ receptors activate ERK through the RAS pathway (Nebigil, C. G., et. al. 5-hydroxytryptamine 2B receptor regulates cell-cycle progression: cross-talk with tryrosine kinase pathways. *Proc. Natl. Acad. Sci. USA.* 2000, 97, 2591-2596); Hershenson, M. B., et. al. Histamine antagonizes serotonin and growth factor-induced mitogen-activated protein kinase activation in bovine tracheal smooth muscle cells. J. Biol. Chem. 1995, 270, 19908-19913); Banes, A., et. al., Mechanism of 5-hydroxytryptamine 2A receptor activation of the mitogen-activated protein kinase pathway in vascular smooth muscle. *J. Pharmacol. Exp. Ther.* 1999, 291, 1179-1187).

Fibrosis is an important key feature of small intestinal neuroendocrine tumor (SI-NETs) both in local peritumoral tissue and systemic (cardiac) sites. 5-HT is a well known inducer of fibrosis. The growth factors regulating fibrosis and proliferation in the tumor microenvironment and mechanisms are unclear. It has been shown that blocking 5-HT$_{2B}$ receptors on tumor cells inhibit SI-NET 5-HT release and in turn fibroblast activation in the tumor microenvironment. In the 5-HT$_{2B}$ expressing SI-NET cell line, KRJ-1, a 5-HT$_{2B}$ antagonist has been shown to inhibit proliferation and 5-HT secretion and decreased ERK1/2 phosphorylation and profibrotic growth factor synthesis and secretion (transforming growth factor beta-1 {TGFβ1}), connective tissue growth factor (CTGF) and fibroblast growth factor (FGF2). The 5-HT$_{2B}$ antagonist was also found to significantly decrease 5-HT release, TGFβ1, CTGF, and FGF2.

Blocking the 5-HT$_{2B}$ receptor with a 5-HT$_{2B}$ antagonist is an effective antiproliferative and antifibrotic strategy for SI-NETs because it inhibits tumor micronvironment fibroblasts as well as NET cells. Use of 5-HT$_{2B}$ receptor antagonists offers a possible effective therapeutic intervention to prevent tumor progression, fibrosis, and metastasis in the neuroendocrine neoplasia. It may also have therapeutic use in other fibrotic processes associated with neuroendocrine cell dysregulation such as Crohn's disease (Kidd, M., et. al. ILlbeta- and LPS-induced serotonin secretion is increased in EC cells derived from Crohn's disease, Neurogastroenterology and Motility, 2009; 21, 439-450).

The compounds of this invention represented by formula I are valuable in the prevention, treatment or cure of various disease conditions regulated directly or indirectly by the inhibition of 5-HT receptors (antagonist) or activation of the neurotransmitter serotonin 5-HT (partial or full agonists). These diseases include chronic liver diseases, liver cirrhosis, liver fibrosis, hepatocellular carcinoma, renal cell carcinoma, kidney cancer, brain cancer, breast cancer, blood cancer, colorectal cancer, lung cancer, liver cancer, ovarian cancer, pancreas cancer, prostate cancer, stomach cancer, testicular cancer, uterus cancer, intestinal cancer, skin cancer, and other forms of cancer, carcinoid tumors, tumor progression, metastasis and fibrosis in the neuroendocrine neoplasia, fibrotic processes associated with neuroendocrine cell dysregulation for example Crohn's disease, chronic kidney disease, Focal Segmental Glomerulosclerosis (FSGS), proteinuria, pulmonary arterial hypertension, pulmonary hypertension associated with chronic obstructive pulmonary disease (COPD), right ventricular hypertrophy, pulmonary vascular remodeling, asthma, cystic fibrosis, hypertension, ischemic stroke, angina pectoris, congestive heart failure, acute myocardial infarction, arrhythmia, arterial fibrillation, neurodegenerative diseases, age-related macular degeneration, Alzheimer's disease, dementia, cognition impairment, memory decline, schizophrenia, dementia associated with Parkinson's and Huntington's disease, progressive supranuclear palsy (PSP), Parkinson disease, Huntington disease, Pick's disease and Jacob disease, gastrointestinal disorders including irritable bowel syndrome, gastroesophageal reflux disease, Crohn's disease, gastric emptying disorders, gastritis, emesis, nausea, vomiting, prokinesia, non-ulcer dyspepcia, urinary incontinence, eating disorders, bulimia, anorexia, obesity, constipation, and respiratory depression, stress disorders, post-traumatic stress disorder, acute stress disorder, delirium, anxiety, depression, attention deficit disorder, attention deficit hyperactivity disorder (ADHD), bipolar depression, epilepsy, age-related macular degeneration, Down's syndrome, pain, migraine, panic disorders, social phobia, animal phobias, and obsessive compulsive disorders, substance-related disorders including dependence and abuse, intoxication, withdrawal, and delirium arising from the use of alcohol, amphetamines, cannabis, cocaine, hallucinogens, inhalants, nicotine, opioids, hypnotics, and anxiolytics, demyelinating diseases including multiple sclerosis, ALS, peripheral neuropathy, postherpetic neurolegia, cereberal vascular disorders, acute or chronic cereberovascular damage, cerebral infarction, subarachanoid hemorrhage, and cerebral edema, bronchoconstriction, vasodilation, smooth muscle contraction, brain disorders, vascular disorders, blood flow disorders as a result of vasodilation and vasospastic diseases such as angina, vascular headache, Reynaud's disease, pulmonary hypertension, systemic hypertension, scleroderma, ischemia, sexual dysfunction, erectile dysfunction, cardiovascular system regulation, prophylaxis and treatment of cerebral infarct, stroke, cerebral ischemia; metabolic diseases such as obesity, diabetes, as well as the treatment of diseases of the intestinal tract, stress-related somatic disorders, bladder function disorders such as cystitis, stress-related urinary incontinence, urinary incontinence post prostate cancer-surgery, reflex sympathetic dystrophy including shoulder/hand syndrome, bladder function disorders such as cystitis, sexual dysfunction, erectile dysfunction, and any nociception, pain or migraine associated with the above mentioned conditions as well as a disease state modulated directly or indirectly with 5-HT receptors or kinases pathways including Breakpoint Cluster Region (BCR)-Abelson Tyrosine Kinase (ABL), Epidermal Growth Factor Receptor (EGFR), Platelet-Derived Growth Factor (PDGF),Vascular Endothelial Growth Factor (VEGF), Human Epidermal Growth Factor (Her),Extracellular Signal-Regulated Kinase (ERK), Proto-oncogene Tyrosine Protein Kinase (Sarc), Mitogen Activated Protein (MAP) Kinase, proto-oncogene receptor tyrosine (Met), TYRO3 (Protein Tyrosine Kinase 3), Maternal Embryonic Leucine zipper Kinase (MELK), Mammalian Sterile zo-like Kinase 4 (MST4), Feline Sarcoma and Feline Sarcoma-relatede (FPS/FER)Tyrosine Kinase, Cancer Osaka Thyroid Kinase aka MAPK-38 (COT), Pyruvate Dehydrogenase Kinase Isoform-2 (PDK2), Receptor d Origine Nantais Kinase (RON), NAUK-2, Mixed-Lineage Protein Kinase 3 (MLK3), Protein Kinase N3 (PKN3), and other family members.

The compounds of the invention disclosed here may be useful in the treatment, prevention or cure of chronic liver disease, including but not limited to liver cirrhosis, and liver fibrosis.

The compounds of this invention may also be useful in the treatment, prevention or curing hepatocellular carcinoma, liver cancer or cancer metastasis in the liver.

The compounds of this invention may also be useful in the treating, preventing or curing various other forms of cancers regulated by various protein tyrosine kinases since the 5-HT second messenger intracellular signal transduction involves various protein tyrosine kinases cascade.

The compounds of this invention may have therapeutic use in treating, preventing or curing various forms of cancer including but not limited to kidney cancer, colorectal cancer, breast cancer, prostate cancer, ovarian cancer, lung cancer, skin cancer, head and neck cancer, solid tumors and non-small cell lung cancer, carcinoid tumors or teratocarcinoma.

The compounds of this invention may have therapeutic use in preventing treating or curing cognition or memory dysfunction due to Alzheimer's disease, progressive supranuclear palsy, PSP, (a form of frontotemporal demential (FTD), Parkinson disease, psychosis, Huntington disease, cognitive impairment (CMI), CMI associated with schizophrenia, post-tramatic syndrome, depression, stroke, stress, surgery, congestive heart failure and myocardial infarction.

The compounds of this invention may have therapeutic uses in treating, preventing and curing obesity and/or diabetes.

The compounds of this invention may have therapeutic uses in treating, preventing and curing chronic kidney disease.

These compounds may also have applications in the treatment of gastrointestinal disorders including irritable bowel syndrome, gastroesophageal reflux disease, Crohn's disease, gastric emptying disorders, gastritis, emesis, nausea, vomiting, prokinesia, non-ulcer dyspepcia, urinary incontinence, eating disorders, bulimia, anorexia, obesity, constipation, constipation, and respiratory depression, stress disorders, post-traumatic stress disorder, acute stress disorder, delirium, anxiety, general anxiety disorders, depression, major depressive disorder, biopolar depression, attention deficit hyperactivity disorder (ADHD), psychosis, epilepsy, age-related macular degeneration, Down's syndrome, pain, migraine, panic disorders, social phobia, animal phobias, and obsessive compulsive disorders.

The compounds of formula I may also be valuable in substance-related disorders including dependence and abuse, intoxication, withdrawal, and delirium arising from the use of alcohol, amphetamines, cannabis, cocaine, hallucinogens, inhalants, nicotine, opioids, hypnotics, and anxiolytics.

These compounds of formula I may also be useful for the prevention and treatment of demyelinating diseases including multiple sclerosis, ALS, peripheral neuropathy, post herpetic neuralgia, cerebral vascular disorders, acute or chronic cerebrovascular damage, cerebral infarction, subarachnoid hemorrhage, and cerebral edema.

In addition, compounds of the invention may be used for the treatment of bronchoconstriction, vasodilation, smooth muscle contraction, brain disorders, vascular disorders, blood flow disorders as a result of vasodilation and vasospastic diseases such as angina, vascular headache, Reynaud's disease, pulmonary hypertension, and systemic hypertension; neuropathological diseases such as Alzheimer's diseases, Parkinson's disease, Huntington's disease; cardiovascular system regulation, prophylaxis and treatment of cerebral infarct, stroke, cerebral ischemia; as well as the treatment of diseases of the intestinal tract.

The compounds of the present invention may also be useful in the treatment of stress-related somatic disorders, bladder function disorders such as cystitis, stress-related urinary incontinence, urinary incontinence post prostate cancer-surgery, reflex sympathetic dystrophy including shoulder/hand syndrome, bladder function disorders such as cystitis, and any nociception, pain or migraine associated with the above mentioned conditions.

The compounds of this invention may be useful in all diseases mentioned above when administered orally, intravenously, subcutaneously, topically, or inhalation, via nasal route, or as a suppository for rectal administration, or as a transdermal patch.

The compounds of the present invention may be administered for treating or preventing or curing a disease, as a single therapeutic agent or in combination with other available medicines known to treat diseases mentioned above by another mechanism-of-action to increase efficacy and/or safety and/or to lower dose level to minimize or eliminate adverse side effects associated with one or more therapeutic agents.

DETAILED DESCRIPTION OF THE INVENTION

The present invention is concerned with deuterium-enriched pyrimidine compounds of formula I, their derivatives, non-racemic isomers, enantiomers, diastereomers, mixtures, solvates and pharmaceutical salts thereof,

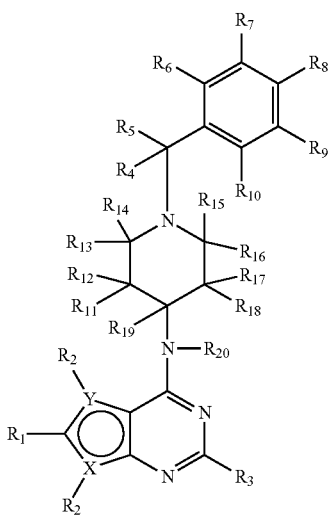

wherein, when X=S or O, Y is C or N; when Y is C, it is substituted with $R_2$;

when Y=S or O, X is C or N; when X is C, it is substituted with $R_2$;

$R_1$ is D (Deuterium), F, Cl, $CD_3$, CN, $CF_3$, $CD(CD_3)_2$, i-Bu($d_{1-9}$), $O(CD_2CD_2CD_3)$, Phenyl-$d_5$, 4-F-Ph-$d_4$, deuterated-thiophenyl-$d_3$, deuterated furanyl-$d_3$, deuterated thiazolyl-$d_3$, deuterated-pyridyl ($C_5D_4$), deuterated-imidazolyl-$d_3$, deuterated-pyrrolyl-$d_4$;

$R_2$ is D, F, Cl, $CD_3$, $CF_3$, CN, $OCF_3$, $OCD_3$, $CD(CD_3)_2$, $C_6D_5$, 4-F—$C_6D_4$, 3-F—$C_6D_4$, 2-F—$C_6D_4$; deuterated-thiophenyl-$d_3$, deuterated furanyl-$d_3$, deuterated thiazolyl-$d_3$, deuterated-pyridyl ($C_5D_4$), deuterated-imidazolyl-$d_3$, deuterated-pyrrolyl-$d_4$;

$R_3$ is H, D, $CD_3$, $NHCD_3$, $NHCD_2CD_3$, $NHCD_2CD_2CD_3$, $NHCD_2CD_2CD_2CD_3$, $NHCD_2CD_2CD_2CD_2CD_3$; CN, F, Cl, $OCD_3$, $C_6D_5$, pyridyl-$d_4$, $R_4$ and $R_5$ independently are D or H, $CD_3$, $CH_3$;

$R_6$, $R_7$, $R_8$, $R_9$ and $R_{10}$ independently are D, H, F, Cl, CN, $CD_3$, $CF_3$, $OCD_3$, $OCF_3$, $OCD_2CD_2CD_3$, $CONDCD_3$, $CON(CD_3)_2$, $SO_2CD_3$, $R_{11}$, $R_{12}$, $R_{13}$, $R_{14}$, $R_{15}$, $R_{16}$, $R_{17}$, $R_{18}$, and $R_{19}$ independently are D, F, H;

$R_{20}$ is D, H; enantiomers, diastereomers, mixtures and pharmaceutical salts thereof.

Pharmaceutically acceptable salts selected from the group consisting of salts of acids including HCl, HBr, HI, acetic, trifluoroacetic, citric, maleic (maleate), fumaric (fumarate), ascorbic, benzoin, methanesulfonic, benzenesulfonic, bicarbonic, carbonic, ethane disulfonic, edetic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenyllacetic, phosphoric, polygalacturonic, propionic, salicyclic, stearic, subacetic, succinic, sulfamic, sulfanilic, sulfuric, tannic, tartaric, tolouenesulfonic, methylsulfonic and p-bromobenzenesulfonic.

The compounds of formula I have antagonist or agonist activity for serotonin receptor subtypes 2B (5-HT$_{2B}$ receptor), 5-HT$_{2A}$ receptor, 5-HT$_{1A}$ and dopamine ($D_1$, $D_2$, $D_3$ and $D_4$) receptors, protein tyrosine kinases including but not limited to EDGFR, PDGFR, VEGFR, ERK, MET, MAP, and these compounds and pharmaceutical salts thereof can accordingly be used for the treatment of diseases associated with these receptors and kinases, especially cancer including brain cancer, breast cancer, blood cancer, colorectal cancer, lung cancer, liver cancer, ovarian cancer, pancreas cancer, prostate cancer, stomach cancer, testicular cancer, uterus cancer, intestinal cancer, skin cancer, and other forms of cancer; tumor progression, metastasis and fibrosis in the neuroendocrine neoplasia, fibrotic processes associated with neuroendocrine cell dysregulation for example Crohn's disease, pulmonary arterial hypertension, pulmonary hypertension associated with chronic obstructive pulmonary disease (COPD), right ventricular hypertrophy, pulmonary vascular remodeling, asthma, cystic fibrosis, hypertension, ischemic stroke, angina pectoris, congestive heart failure, arrhythmia, arterial fibrillation, neurodenerative diseases, Alzheimer's disease, dementia, cognition impairment, memory decline, progressive supranuclear palsy, PSP, (a form of frontotemporal demential (FTD), schizophrenia, dementia associated with Parkinson's and Huntington's disease, Pick's disease and Jacob disease, gastrointestinal disorders including irritable bowel syndrome, gastroesophageal reflux disease, Crohn's disease, gastric emptying disorders, gastritis, emesis, nausea, vomiting, prokinesia, non-ulcer dyspepcia, urinary incontinence, feeding disorders, bulimia, anorexia, obesity, constipation, constipation, and respiratory depression, stress disorders, post-traumatic stress disorder, acute stress disorder, delirium, anxiety, depression, biopolar depression, epilepsy, Down's syndrome, pain, migraine, panic disorders, social phobia, animal phobias, and obsessive compulsive disorders, substance-related disorders including dependence and abuse, intoxication, withdrawal, and delirium arising from the use of alcohol, amphetamines, *cannabis*, cocaine, hallucinogens, inhalants, nicotine, opioids, hypnotics, and anxiolytics, demyelinating diseases including multiple sclerosis, ALS, peripheral neuropathy, postherpetic neurolegia, cereberal vascular disorders, acute or chronic cereberovascular damage, cerebral infarction, subarachanoid hemorrhage, and cerebral edema, bronchoconstriction, vasodilation, smooth muscle contraction, brain disorders, vascular disorders, blood flow disorders as a result of vasodilation and vasospastic diseases such as angina, vascular headache, Scleroderma, Reynaud's disease, pulmonary hypertension, and systemic hypertension; neuropathological diseases such as Alzheimer's diseases, Parkinson's disease, psychosis, Huntington's disease; cardiovascular system regulation, prophylaxis and treatment of cerebral infarct, stroke, cerebral ischemia; obesity, diabetes, eating disorders, chronic kidney disease, as well as the treatment of diseases of the intestinal tract, stress-related somatic disorders, bladder function disorders such as cystitis, stress-related urinary incontinence, urinary incontinence post prostate cancer-surgery, reflex sympathetic dystrophy including shoulder/hand syndrome, bladder function disorders such as cystitis, and any nociception, pain or migraine associated with the above mentioned conditions.

A preferred group of compounds of formula I are those in which,

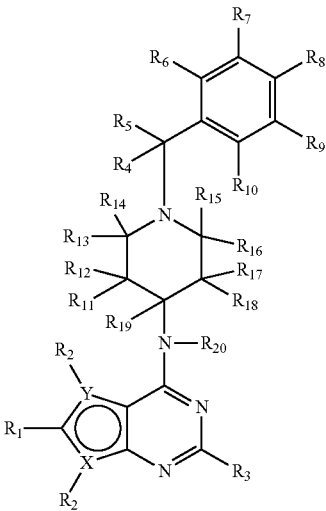

when X=S, Y is C or N; when Y is C, it is substituted with R$_2$;
when Y=S, X is C or N; when X is C, it is substituted with R$_2$;
R$_1$ is D (Deuterium), F, Cl, CD$_3$, CF$_3$, CN, CD(CD$_3$)$_2$, Phenyl-d$_5$, 4-F-Ph-d$_4$, deuterated-thiophenyl-d$_3$, deuterated furanyl-d$_3$, deuterated thiazolyl-d$_3$, deuterated-pyridyl (C$_5$D$_4$), deuterated-imidazolyl-d$_3$, deuterated-pyrrolyl-d$_4$;
R$_2$ is D, F, Cl, CF$_3$, CN, CD$_3$, CD(CD$_3$)$_2$;
R$_3$ is H, D;
R$_4$ and R$_5$ are D, H, CD$_3$;
R$_6$, R$_9$ and R$_{10}$ are D, H, F, CN, CF$_3$;
R$_7$ is CN, F, CF$_3$, CD$_3$;
R$_8$ is F, CN, CF$_3$;
R$_{11}$, R$_{12}$, R$_{17}$, R$_{18}$, and R$_{19}$ are D;
R$_{13}$, R$_{14}$, R$_{15}$, R$_{16}$ are H or D;
R$_{20}$ is D, H;
and salts thereof.

One of the objectives of the present invention is to provide deuterium enriched compounds of formula I or a pharmaceutically acceptable salt thereof.

It is another objective of the present invention to provide pharmaceutical compositions comprising a pharmaceutically acceptable carrier and a therapeutically effective amount of at least one of the deuterium enriched compounds of the present invention as a pharmaceutically acceptable salt thereof.

It is another object of the present invention is to provide a method for the prevention and treatment of chronic liver diseases including liver cirrhosis, liver fibrosis and liver cancer.

It is another object of the present invention is to provide a therapeutic agent (drug or medicine, method for treatment) for the prevention and treatment of cancer including hepatocellular carcinoma, liver cancer, renal cell carcinoma, kidney cancer, colorectal cancer, brain cancer, breast cancer, blood cancer, lung cancer, thyroid cancer, ovarian cancer, pancreas cancer, prostate cancer, stomach cancer, testicular cancer, uterus cancer, intestinal cancer, skin cancer, and other forms of cancer, carcinoid tumors, teratocarcinoma, tumor progression, neuroendocrine tumors, metastasis and fibrosis in the neuroendocrine neoplasia, fibrotic processes comprising administering a pharmaceutically effective dose of a deuterium-enriched compound of formula I, Another aspect of the invention is to provide a method for the prevention and treatment of tumor progression or proliferation in various cancers mentioned above.

Another aspect of the invention is to provide a method for the prevention and treatment of metastasis of cancer tumors in various forms of cancer mentioned above.

Another aspect of the invention is to provide a method for the prevention and treatment of fibrosis in the neuroendocrine neoplasia.

Another aspect of the invention is to provide a method for the prevention and treatment of fibrotic processes associated with neuroendocrine cell dysregulation for example Crohn's disease.

Another object of the present invention is to provide a method for the prevention and treatment of Parkinson's disease.

Another object of the present invention is to provide a method for the prevention and treatment of psychosis.

Another object of the present invention is to provide a method for the prevention and treatment of Alzheimer's disease.

Another object of the present invention is to provide a method for the prevention and treatment of mild to moderate cognitive impairment.

Another object of the present invention is to provide a method for the prevention and treatment of progressive supranuclear palsy, PSP, (a form of frontotemporal demential (FTD).

Another object of the present invention is to provide a method for the treatment or prevention of obesity, diabetes and/or eating disorders.

Another object of the present invention is to provide a method for the treatment or prevention of age-related macular degeneration (AMD).

Another object of the present invention is to provide a method for the prevention and treatment of pulmonary arterial hypertension (PAH).

Another object of the present invention is to provide a method for the prevention and treatment of pulmonary hypertension associated with chronic obstructive pulmonary disease (COPD).

It is another object of the present invention to provide a method for the prevention and treatment of right ventricular hypertrophy.

It is another object of the present invention to provide a method for the prevention and treatment of pulmonary vascular remodeling.

It is another object of the present invention to provide a method for the prevention and treatment of scleroderma.

It is another object of the present invention to provide a method for the prevention and treatment of resistance hypertension.

It is another object of the present invention to provide a method for the prevention and treatment of hypertension, angina pectoris, resistance hypertension and congestive heart failure.

It is another object of the present invention is to provide a method for the prevention and treatment of attention deficit hyperactivity disorder and attention deficit disorder.

It is another object of the present invention is to provide a method for the prevention and treatment of epilepsy.

It is another object of the present invention is to provide a method for the prevention and treatment of male erectile dysfunction.

It is another object of the present invention is to provide a method for the prevention and treatment of chronic kidney disease.

It is another object of the present invention to provide a method for the prevention and treatment of all disease regulated directly or indirectly by 5-HT receptors and protein tyrosine kinases, comprising administering to a host in need of such treatment a therapeutically effective amount of at least one of the compounds of the present invention or a pharmaceutically acceptable salt thereof.

It is another object of the present invention to provide a method for the prevention and treatment of all disease regulated directly or indirectly by 5-HT receptors and protein tyrosine kinases (as discussed above) comprising administering to a host in need of such treatment a therapeutically effective amount of at least one of the compounds of the present invention as a single agent and/or as a combination therapeutic agent (medicament or drug) with other available drugs with a different mechanism-of-action than the 5-HT receptor modulation.

It is another object of the present invention to provide a novel deuterium-enriched pyrimidine compounds of formula I, pharmaceutically acceptable salts thereof for use as therapeutic agents.

It is another object of the present invention to provide a novel deuterium-enriched pyrimidine compounds of formula I, pharmaceutically acceptable salts thereof for use as prophylactic agents.

It is another object of the present invention to provide a novel deuterium-enriched pyrimidine compounds of formula I, pharmaceutically acceptable salts thereof for use as therapeutic agents administered as a single therapeutic agent or given in combination with another clinically approved therapeutic agent.

The combination agents may be selected from the therapeutic agents discussed below:

Endothelin antagonists such as bosentan, ambrisentan, sitaxentan, macitentan and others for the treatment and prevention of pulmonary arterial hypertension, pulmonary hypertension associated with COPD, right ventricular hypertrophy, pulmonary vascular remodeling, and other pulmonary diseases.

Phosphodiesterase-V (PDE-V or PDE-5) inhibitors such as sildenafil, tadalafil, vardenafil, and others for the treatment and prevention of pulmonary arterial hypertension, pulmonary hypertension associated with COPD, right ventricular hypertrophy, pulmonary vascular remodeling, and other pulmonary diseases, erectile dysfunction, angina and stroke.

Imitanib (Gleevec or Glivec), a tyrosine kinase inhibitor (bcr-abl, c-kit, PDGFR) for the treatment and prevention of pulmonary arterial hypertension, smooth muscle hypertrophy and hyperplasia of the pulmonary vasculature, portopulmonary hypertension, and related pulmonary and cardiovascular diseases.

Angiotensin-II (A-II) receptor antagonist such as losartan, valsartan, irbesartan, candensartan for the prevention and treatment of hypertension, congestive heart failure, left ventricular hypertrophy, myocardial infarction, congestive heart failure, angina, chronic kidney disease and diabetic nephropathy.

Multiple kinase (VEGF, PDGF, MAP, Met, Erk, Raf, c-Raf, B-Raf) inhibitors such as Sorafenib (Nexavar), a non-selective protein tyrosine kinase inhibitor of VEGFR, PDGFR, MAP kinase inhibitor, Raf/Mek, Erk pathway), raf kinases (C-Raf and B-raf), for the treatment, prevention and cure of liver cancer (hepatocellular carcinoma), kidney cancer (advanced renal cell carcinoma, RCC), thyroid cancer, lung cancer, and brain cancer, breast cancer, colorectal cancer, and gastrointestinal stromal tumors (GIST).

Sorafenib (Nexavar), a non-selective protein tyrosine kinase inhibitor of VEGFR, PDGFR, MAP Kinase inhibitor, Raf/Mek, Erk pathway), raf kinases (C-Raf and B-raf), for the treatment, prevention and cure of liver cancer (hepatocellular carcinoma), kidney cancer (advanced renal cell carcinoma, RCC), thyroid cancer, lung cancer, and brain cancer, breast cancer, colorectal cancer, and gastrointestinal stromal tumors (GIST).

Regorafenib, a non-selective protein tyrosine kinase inhibitor of VEGF (or VEGFR), PDGF (or PDGFR), MAP Kinase inhibitor, Raf/Mek, Erk pathway), raf kinases (C-Raf and B-raf), for the treatment, prevention and cure of metastatic colorectal cancer, liver cancer (hepatocellular carcinoma), kidney cancer (advanced renal cell carcinoma, RCC), thyroid cancer, lung cancer, and brain cancer, breast cancer, colorectal cancer, and gastrointestinal stromal tumors (GIST).

Imitanib (Geevec or Glivec), a tyrosine kinase inhibitor (bcr-abl, c-kit, PDGFR) for the treatment and prevention of various forms of cancer including chronic myelogenous leukemia, gastrointestinal stromal tumors (GIST), progressive plexiform neurofinromas associated with neurofibromatosis type 1, relapsed refractory Philadelphia chromosome (Ph)-positive CML, myelodisplastic/myeloproliferative diseases associated with platelet-derived growth factor recptor (PDGFR) gene rearrangement, aggressive systemic mastocytosis, chronic eosinophilic leukemia (CEL), hypereosinophilic syndrome (HES), recurrent and/or metastatic dermatofibrosarcoma protuberans.

Imitanib for the treatment of Alzheimer's disease and/or mild cognitive impairment associated with schizophrenia and age-related dementia by halting or slowing down the production and accumulation of the neurotoxic beta-amyloid plaque by binding to the γ-secretase activating protein (GSAP).

Erlotinib (Tarceva), a tyrosine kinase (Herl/EGFR, epidermal growth factor receptor) inhibitor, for the treatment and prevention of lung cancer, non-small cell lung cancer, pancreatic cancer, solid tumors such as ovarian, colorectal, head and neck, renal cell carcinoma, glioma, and gastrointestinal cancers.

Other kinase inhibitors for combination therapy with compounds of the present invention include Sunitinib, Lapatinib, Matesanib, Tandutanib, Nilotinib, Dasatinib, Bosutinib, Ponatinib, and/or Bafetinib.

Mitotic inhibitors such as Paclitexal (Taxol) for the treatment of various forms of cancer such as breast, lung, ovarian, head, neck, Kaposi's sarcoma, and restenosis.

It is another objective of the present invention to provide the use of a novel compound of formula I or a pharmaceutically acceptable salt thereof for the manufacture of a medicine for the treatment of all forms of cancer, fibrosis, pulmonary arterial hypertension, resistant hypertension, hypertension, congestive heart failure, obesity, diabetes, eating disorders, chronic kidney disease, sexual dysfunction, male erectile dysfunction, anxiety, depression, ADHD, ADD, Alzheimer's, Parkinson's, and Huntington's disease, Schizophrenia and psychosis.

Also provided are various deuterium-enriched compounds of formula I and administering those compounds to a subject in need thereof to treat or prevent a disease condition that is alleviated by treatment with a 5-HT$_{2B}$ (and/or all 5-HT) receptor antagonist, dopamine receptor modulators. Disease conditions that are alleviated by treatment with 5-HT modulators particularly 5-HT$_{2B}$ receptor antagonists include, but are not limited to, e.g., cancer including brain cancer, breast cancer, blood cancer, colorectal cancer, lung cancer, liver cancer, ovarian cancer, pancreas cancer, prostate cancer, stomach cancer, testicular cancer, uterus cancer, intestinal cancer, skin cancer, and other forms of cancer; tumor progression, metastasis and fibrosis in the neuroendocrine neoplasia, fibrotic processes associated with neuroendocrine cell dysregulation for example Crohn's disease, pulmonary arterial hypertension, pulmonary hypertension associated with chronic obstructive pulmonary disease (COPD), right ventricular hypertrophy, pulmonary vascular remodeling, asthma, cystic fibrosis, hypertension, ischemic stroke, angina pectoris, congestive heart failure, arrhythmia, arterial fibrillation, neurodegenerative diseases, Alzheimer's disease, dementia, cognition impairment, memory decline, schizophrenia, dementia associated with Parkinson's and Huntington's disease, Pick's disease and Jacob disease, gastrointestinal disorders including irritable bowel syndrome, gastroesophageal reflux disease, Crohn's disease, gastric emptying disorders, gastritis, emesis, nausea, vomiting, prokinesia, non-ulcer dyspecpia, urinary incontinence, feeding disorders, bulimia, anorexia, obesity, constipation, constipation, and respiratory depression, stress disorders, post-traumatic stress disorder, acute stress disorder, delirium, anxiety, depression, biopolar depression, ADD, ADHD, epilepsy, Down's syndrome, pain, migraine, panic disorders, social phobia, animal phobias, and obsessive compulsive disorders, substance-related disorders including dependence and abuse, intoxication, withdrawal, and delirium arising from the use of alcohol, amphetamines, cannabis, cocaine, hallucinogens, inhalants, nicotine, opioids, hypnotics, and anxiolytics, demyelinating diseases including multiple sclerosis, ALS, peripheral neuropathy, postherpetic neuralgia, cerebral vascular disorders, acute or chronic cereberovascular damage, cerebral infarction, subarachnoid hemorrhage, and cerebral edema, bronchoconstriction, vasodilation, smooth muscle contraction, brain disorders, vascular disorders, blood flow disorders as a result of vasodilation and vasospastic diseases such as angina, vascular headache, Reynaud's disease, pulmonary hypertension, and systemic hypertension; age-related macular degeneration (AMD), neuropathological diseases such as Alzheimer's diseases, Parkinson's disease, Huntington's disease; cardiovascular system regulation, prophylaxis and treatment of cerebral infarct, stroke, cerebral ischemia; as well as the treatment of diseases of the intestinal tract, stress-related somatic disorders, bladder function disorders such as cystitis, stress-related urinary incontinence, urinary incontinence post prostate cancer-surgery, reflex sympathetic dystrophy including shoulder/hand syndrome, bladder function disorders such as cystitis, and any nociception, pain or migraine associated with the above mentioned conditions.

The present invention relates to compounds of formula I, their pharmaceutically acceptable salts, compositions and their use as mono therapy or in combination with existing therapies.

Deuterium (D or $^2$H) is a stable isotope non-radioactive isotope of hydrogen (H) and has an atomic weight of 2.0144. Hydrogen occurs naturally as a mixture of the isotopes $^1$H, D ($^2$H), and T ($^3$H or tritium and the natural abundance of deuterium is 0-0.0156%.

One of ordinary skill in the art recognizes that in all compounds containing H atom, H actually represents a mixture of H and D, within the range of 0-0.0156% of D.

So, compounds with a level of D that has been enriched to be greater than its natural abundance of 0.0156%, should be considered unnatural and as a result novel as compared to their corresponding non-enriched counterparts.

The carbon-hydrogen bonds contain a naturally occurring distribution of hydrogen isotopes, namely $^1$H or protium (about 99.9844%), $^2$H or deuterium (D) (about 0.0156%), and $^3$H or tritium (in the range between about 0.5 and 67 tritium atoms per 1018 protium atoms). Higher levels of deuterium incorporation produce a detectable Kinetic Isotope Effect (Werstiuk, N.H.; Dhanoa, D. S.; Timmins, G. *Can J. Chem.* 1979, 57, 2885; Werstiuk, N.H.; Dhanoa, D. S.; Timmins, G. *Can J. Chem.* 1983, 61, 2403), that could improve the pharmacokinetic, pharmacologic and/or toxicologic parameters of compounds of formula I in comparison to compounds having naturally occurring levels of deuterium and their corresponding hydrogen (protium) analogs. Deuterium as an isostere of hydrogen has been employed in drug design (Meanwell, N. A., Synopsis of some recent tactical application of bio-isosteres in drug design, *J. Med. Chem.* 2011, 54, 2529-2591).

The present invention disclosed herein describes novel compounds of formula I containing higher content of deuterium (>1%), synthesis and uses thereof as 5-HT receptor antagonists and/or inverse agonist for the treatment of diseases in which 5-HT plays role directly or in directly. Suitable modifications of certain carbon-hydrogen bonds into carbon-deuterium bonds generates novel substituted pyrimidine compounds with unexpected and non-obvious improvements of pharmacological, pharmacokinetic and toxicological properties in comparison to the non-isotopically enriched 5-HT$_{2B}$ antagonists, agonists, or inverse agonists. This invention relies on the judicious and successful application of chemical kinetics to drug design. Deuterium incorporation levels in the compounds of the invention are significantly higher than the naturally-occurring levels and are sufficient to induce at least one substantial improvement as described herein. All percentages given for the amount of D present are mole percentages.

"Deuterium enrichment" refers to the percentage of incorporation of deuterium at a given site on the molecule instead of a hydrogen atom. For example, deuterium enrichment of 1% means that in 1% of molecules in a given sample a particular site is occupied by deuterium. Because the naturally occurring distribution of deuterium is about 0.0156%, deuterium enrichment in compounds synthesized using non-enriched starting materials is about 0.0156%.

It can be a significant synthetic challenge to produce 100% deuterium at a specific site of a compound. When 100% deuteration is recited or a deuterium atom is specifically shown in a chemical structure of a compound, a small amount of protium may still be present. Higher levels of deuterium content in a compound can be produced either by Hydrogen-Deuterium (H-D) exchange or by synthesizing the compound for specific deuteration. The H-D exchange is readily achieved in case of H atoms attached to heteroatoms for example in cases of carboxylic acids (COOH), sulfonamides (SO$_2$NH$_2$), alcohols (OH), basic amines (NH$_2$), etc. However, these incorporated D attached to hetero atoms (O, N, 0) etc, readily revert back to H upon exposure to water or any acidic compounds containing H atoms. The preferred deuterium containing compounds are the ones which contain D directly attached to carbon atoms of the structure of the compounds of this invention.

In some embodiments, the deuterium enrichment in the compounds of the present invention is greater than about 4%, 5%, 6%, 7%, 8%, 9% or 10%. In other embodiments, the deuterium enrichment in the compounds of the present invention is greater than about 20%. In further embodiments, the deuterium enrichment in the compounds of the present invention is greater than about 50%. In some embodiments, the deuterium enrichment in the compounds of the present invention is greater than about 70%. In some embodiments, the deuterium enrichment in the compounds of the present invention is greater than about 90%. In some embodiments, the deuterium enriched compounds of the present invention is at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 81%, 83%, 84%, 85%, 86%, 87%, 88%, 89%, 90%, 91%, 92%, 93%, 94%, 95%, 96%, 97%, 98%, 99% and 100%;

The examples provided in the definitions present in this application are non-inclusive unless otherwise stated. They include but are not limited to recited examples. The compounds of the present may have various isomers including all stereoisomers of asymmetric atoms and geometric, tautomeric or rotamers, and all isomers are considered to be part of the present invention. All processes used to prepare compounds of the present invention and intermediates made therein are considered to be part of the present invention.

"Pharmaceutically acceptable salts" refer to derivatives of the disclosed compounds wherein the parent compound is modified by making acid or base salts thereof. Examples of the pharmaceutically acceptable salts include, but not limited to, mineral or organic acid salts of the basic residues. The pharmaceutically acceptable salts include but not limited to salts of the acids, HCl, HBr, HI, acetic, trifluoroacetic, citric, maleic, fumeric, tartaric, ascorbic, benzoin, methanesulfonic, benzenesulfonic, bicarbonic, carbonic, ethane disulfonic, edetic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenyllacetic, phosphoric, polygalacturonic, propionic, salicyclic, stearic, subacetic, succinic, sulfamic, sulfanilic, sulfuric, tannic, tartaric, tolouenesulfonic, methanesulfonic (mesyl), and p-bromobenzenesulfonic.

The preparation of pyrimidine compounds of formula I are illustrated in schemes 1-8 below and in the examples given in Table 1. The schemes and examples are given for the purpose of illustrating the invention and not for limiting the scope or spirit of the invention.

Step A: To a solution of acetaldehyde-$d_4$ 1 (1.2 g) in toluene is added 1.2 equivalent of ethyl cyanoacetate (3.2 g) and ammonium acetate (2.2 g) followed by acetic acid (15 mL). The mixture is refluxed for 6 h under nitrogen using Dean-Stark apparatus. After cooling to room temperature by allowing it to stand, the reaction mixture is concentrated using rotary evaporator under vacuum to remove solvent. To the concentrated residue, is added water and the adduct product 2 is extracted with ethyl acetate. The combined organic layer is dried over anhydrous sodium sulfate or anhydrous magnesium sulfate and concentrated under vacuum. The resulting product 2 (3.0 g) obtained as such is used in step B.

Step B: Morpholine is added to 2 (3 g) in ethanol (5 mL) followed by addition of sulfur in slight excess under nitrogen atmosphere and the suspension is refluxed with stirring for 12 h. After cooling to room temperature, the reaction mixture is concentrated in vacuum and the product 3 is extracted with ethyl acetate from acqueous phase. The combined organic layer was dried over anhydrous sodium sulfate, filtered and the filtrate is concentrated in vacuum and then purified by flash column chromatography using mixture of ethyl acetate and hexane to yield Ethyl 2-Aminothiophene-3-carboxylate-$d_2$ 3 (2.6 g). Mass spectral analysis (MS): m/z: 173.5.

Step C: The ester 3 (0.88 mg) is heated at reflux with deutero ammonium acetate-$d_1$ (100 mg) in 3 ml of formic acid for 8 hrs. The mixture is poured onto ice and the resulting material is filtered and recrystallized from acetone water to give hydroxypyrimidine 4 (0.6 g). Mass spectral analysis (MS): m/z 155.

Step D: The deuterothienopyrimidinol 4 (2 mmol) is heated in thionyl chloride with catalytic amount of N,N-dimethylformamide for 5 hours. The mixture is allowed to cool to room temperature and the excess thionyl chloride is removed under reduced pressure. Excess of ice is added to the mixture and product extracted with dichloromethane. The extracts are dried with anhydrous sodium sulfate, filtered, concentrated and the product purified by flash chromatography over silica gel to yield 5 (0.5 g). Mass spectral analysis (MS): m/z 173.

Step E: To a solution of pyrimidine derivative 5 (0.5 g) was added deuterated acetic acid-$d_4$ (20 mL) and N-chlorosuccinimide (0.2 g) and the mixture was heated for 2.5 h. The reaction mixture was cooled to room temperature and removed acetic acid-$d_4$ in vacuum and the residue was treated with aqueous sodium hydroxide and extracted with dichloromethane. The combined organic extracts were dried over anhydrous MgSO4, filtered and concentrated before purification by flash column chromatography to isolate the 2,6-dichlorothienopyrimidine 6 (0.4 g). Mass spectral analysis (MS) m/z: 205.9.

Scheme 1:

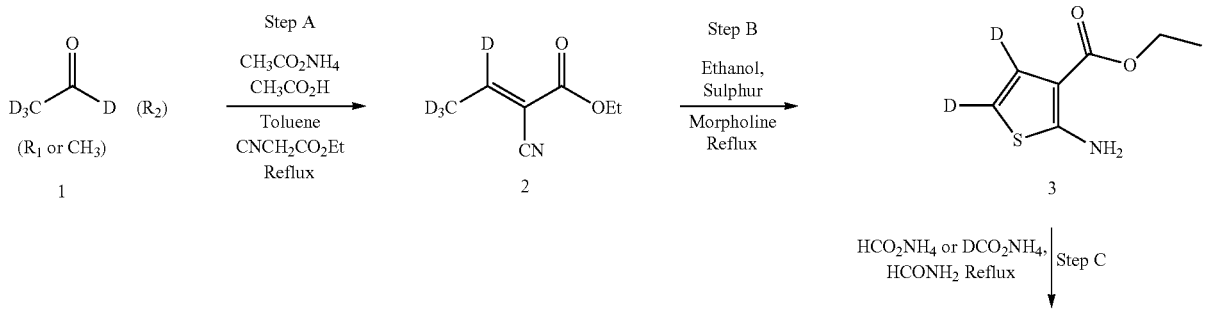

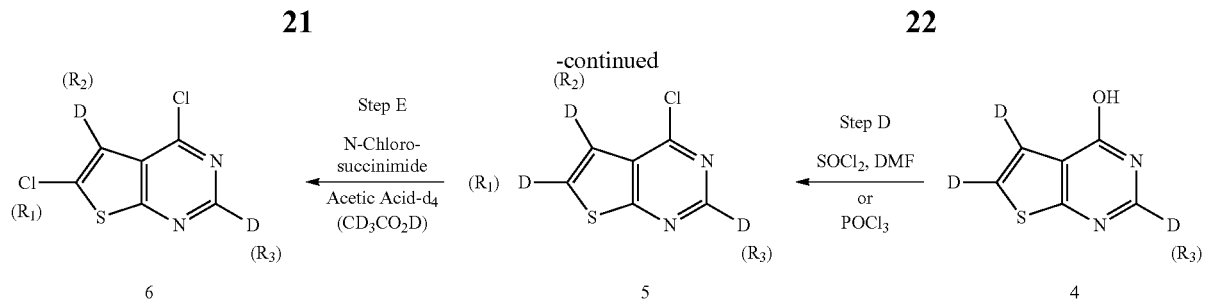

The regioisomeric thienopyrimidine 12 is prepared from deuterated acetaldehyde-d4 as illustrated in Scheme 2.

Step F: To acetaldehyde 7 (0.48 g), DMF, and phosphorus oxychloride (1.2 equiv) is added and the mixture stirred for 5 minutes. Hydroxylamine (1.2 equivalent) is added to the reaction mixture and heated at 50 degree C. for 5 hours. The reaction mixture is cooled to room temperature and poured over to ice. The compound is extracted with methylene chloride and the extracts are dried over anhydrous magnesium sulfate or sodium sulfate, filtered and concentrated under vacuum. The crude product is purified by flash column chromatography to give 8 (0.62 g). MS: m/z 90 (M+1).

Step G: Methyl thioglycolate (1.1 g) and sodium methoxide (2 equiv) in methanol are added to 8 (0.62 g) and the mixture refluxed for 6 hours. The mixture is cooled to room temperature, concentrated to remove solvent and the resulting mixture partitioned between methylene chloride and water. The aqueous portion is further extracted with dichloromethane and ethyl acetate. The combined organic extracts are dried over anhydrous sodium sulfate, filtered and concentrated to a residue. Flash column chromatography of the residue afforded an amino ester 9 (0.8 g).

The intermediate 9 was converted to the pyrimidine derivatives 10, 11 and 12 by using methods describes in Step C, Step D, and Step E, respectively.

Similarly, the amino ester of thiazole, 13, was converted to the 4-hydroxythiozolylpyrimidine 14 and 4-chlorothiazolylpyrimidine 15 as illustrated in Scheme 3 below using step C and Step D as described above.

Scheme 3:

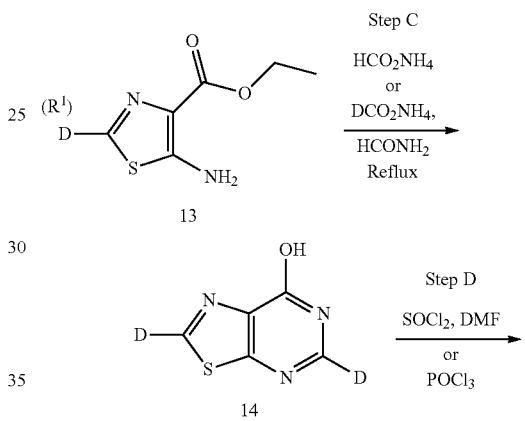

Scheme 2:

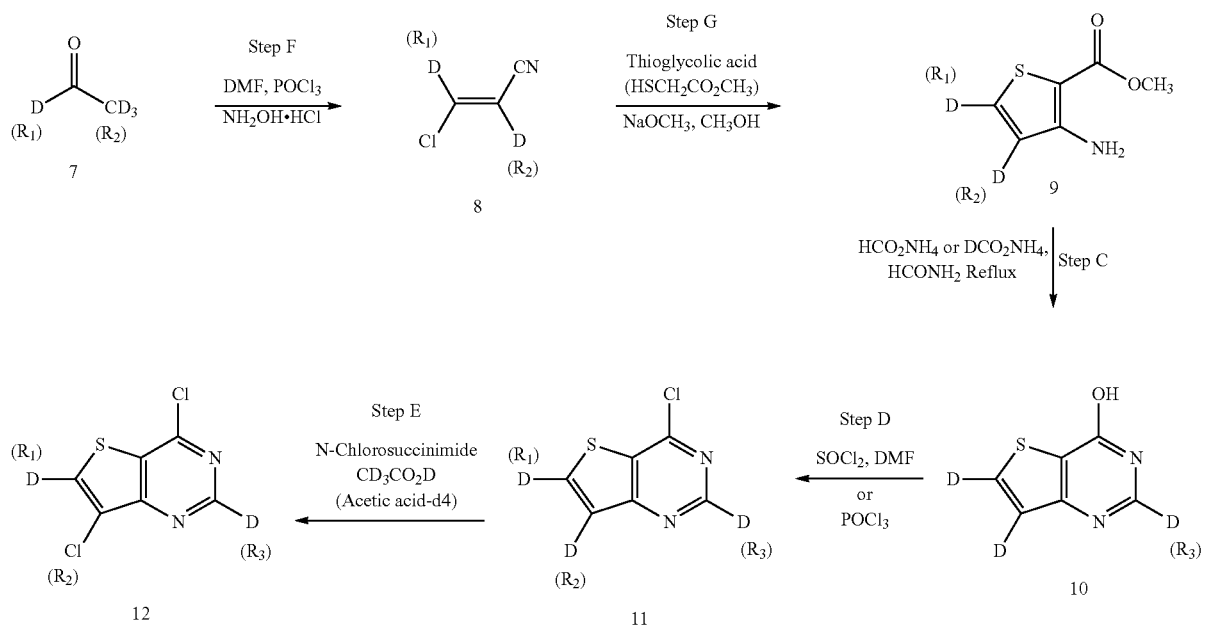

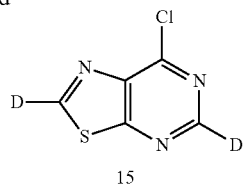

15

Furthermore, the regioisomeric thiazolylpyrimidine 18 is prepared from the corresponding deuterated amino ester 16 as illustrated in Scheme 4 below by utilizing the reaction steps C and D.

Scheme 4:

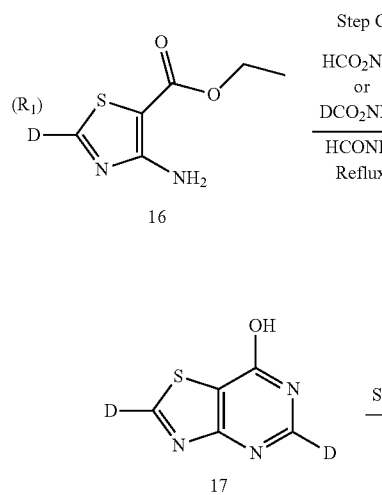

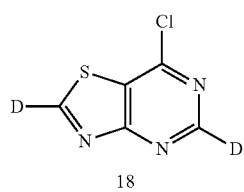

18

Step F: One of three key building blocks of the compounds of formula I of the present invention is the partially or fully deuterated 4-N-Boc-aminopiperidine 20. The preparation of 20 is illustrated in scheme 5 below that employs the use of the reaction step F. The 4-N-Boc-piperidinone is converted to the corresponding amine by reductive amination of 19 with ammonium acetate (NH$_4$OAc) using either sodium triacetoxy borodeuteride [NaBD(OAc)$_3$], or sodium borotetradeuteride [NaBD$_4$], or sodium cyanoborodeuteride [NaBD$_3$CN], as reducing agents in dicholoroethane or dicholoromethane or DMF or tetrahydrofuran (THF) and water (H$_2$O). To a solution of 0.2 g of 4-N-Boc-(2,2,6,6-tetradeuteropiperidinone) 19 (R$_{11}$, R$_{12}$, R$_{17}$, R$_{18}$ are D; R$_{13}$, R$_{14}$, R$_{15}$, R$_{16}$ are H) in DCE and AcOH is added$_1$ [2 equiv of NaBD(OAc)$_3$] and the reaction mixture stirred for 2 h. The mixture was concentrated and basified with NaHCO$_3$ and saturated with NaCl and the resulting mixture is extracted with methylene chloride. The organic solvent extracts were concentrated in vacuo and the product isolated by flash column chromatography to yield 20 (0.12 g).

Scheme 5:

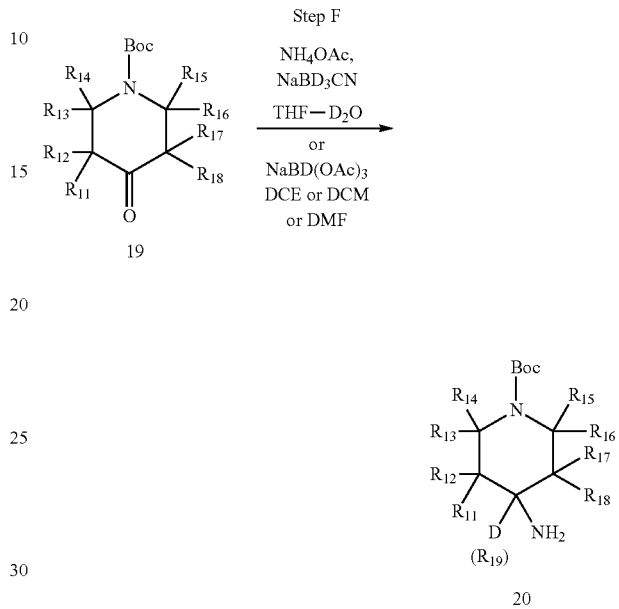

Ac = COCH$_3$ (Acetyl)
DCE = Dichloroethane
DCM = Dichloromethane
DMF = N, N-Dimethylformamide Step G: Diisopropyl ethylamine (Hunigs base) is added to a solution of 4-N-Boc-aminopiperidine-d$_5$, 20 (0.22 g) in acetonitrile (3 ml) followed by addition of 6 (1 equiv). The reaction mixture is refluxed for 24 h. Acetonitrile is removed in vacuo and the resulting residue is dissolved in ethyl acetate (25 ml) and the solution washed with aqueous (aq.) saturated solution of sodium bicarbonate and saturated aqueous solution of sodium chloride (brine). The organic phase is dried over anhydrous MgSO$_4$, concentrated in vacuo and purified by flash column chromatography to give N-Boc protected 21, which in turn is treated with TFA in CH$_2$Cl$_2$ for 2-3 h or with HCl in ether for 12 h to give the crude amine 21. The mixture containing 21 is concentrated in vacuo, treated the residue with aqueous NaHCO$_3$ solution and aqueous solution of NaCl. The organic product was extracted with ethyl acetate and dicholoromethane and the combined organic solvent extracts washed with brine, dried over anhydrous MgSO$_4$, filtered and concentrated in vacuo. The resulting material is purified to afford 21 (0.15 g). MS: m/z 276 (M+1).

Similarly, the regioisomeric thienopyrimidine 22 (m/z 276 M+1) is prepared from 12 and 20 by using Step H. The regioisomeric thiazolylpyrimidines, 23 (m/z 278 M+1) and 24 (m/z 278 M+1) are also prepared in a similar manner by using Step 0 and Step J from their precursors and 20, and 18 and 20, respectively as illustrated in Scheme 6.

Scheme 6:
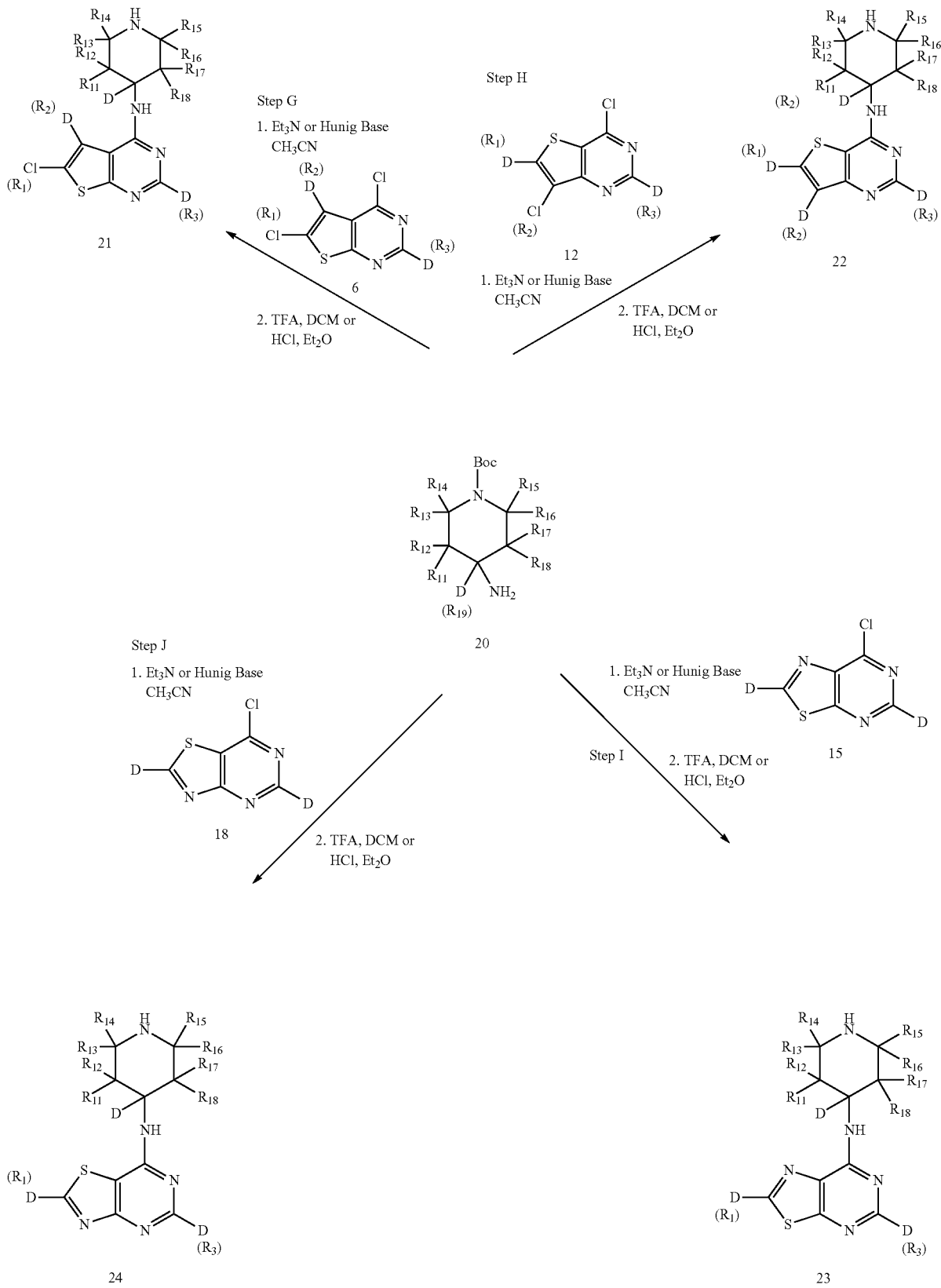

Step K: The 4-aminopiperidine-2-chlorothienopyrimidines 21 and 22 are also prepared from the corresponding N-Boc derivatives 25 and 26, respectively as shown in Scheme 7 by step K as described in Step E of scheme 1.

Scheme 7:

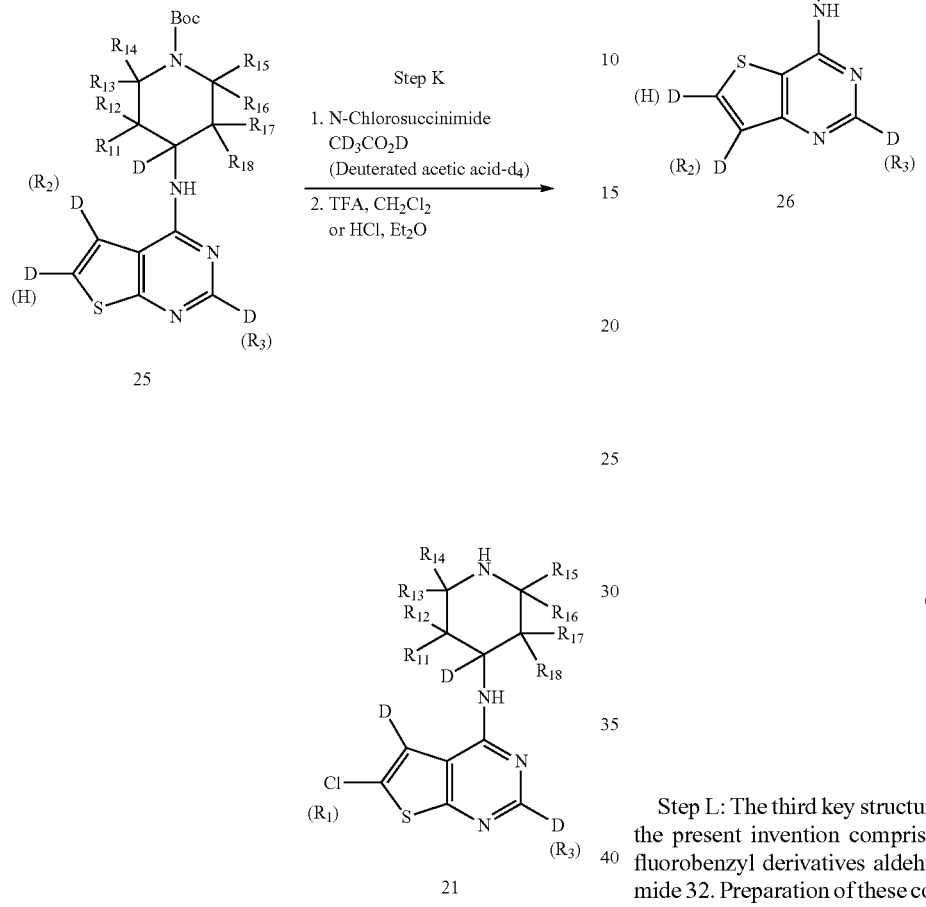

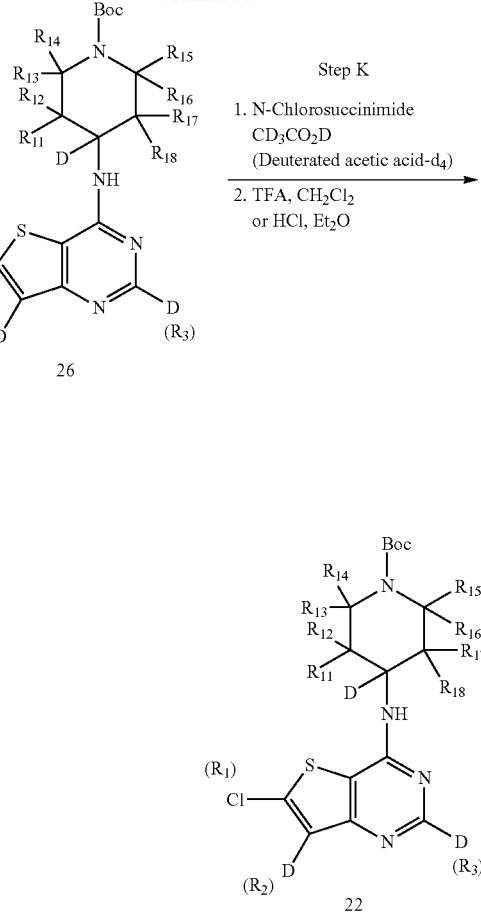

Step L: The third key structural moiety of the compound of the present invention comprise the deuterated 3-cycano-4-fluorobenzyl derivatives aldehydes 29 and 30 and aryl bromide 32. Preparation of these compounds is shown in Scheme 8 below.

Scheme 8:

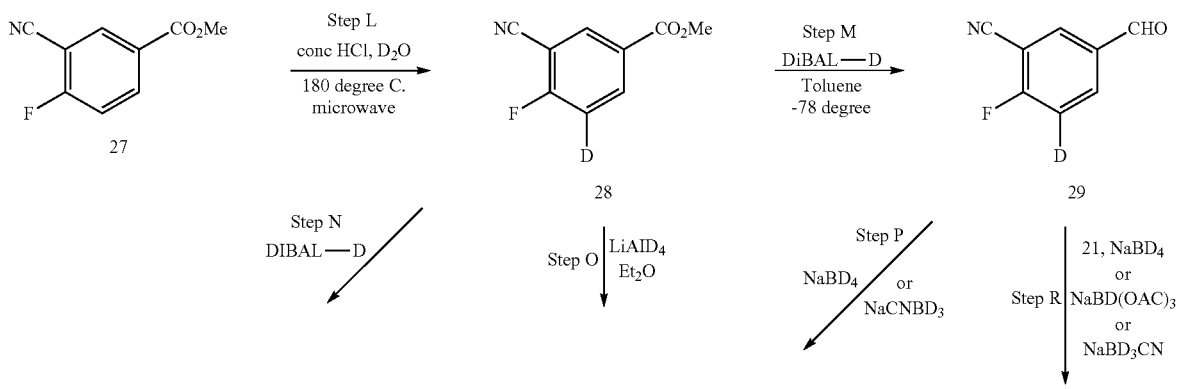

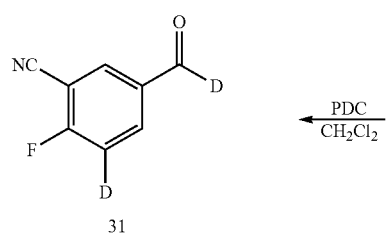
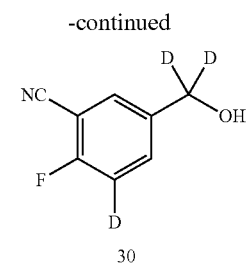
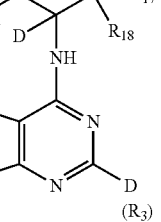
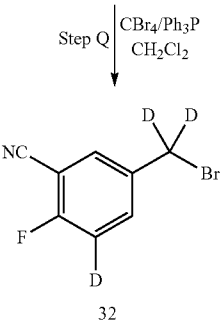
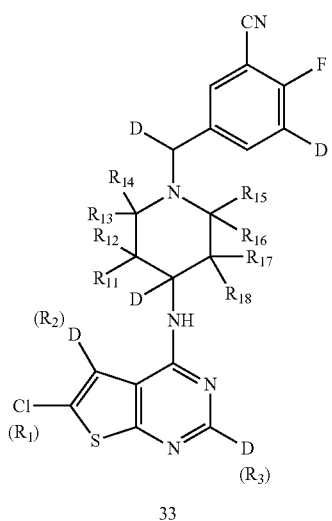
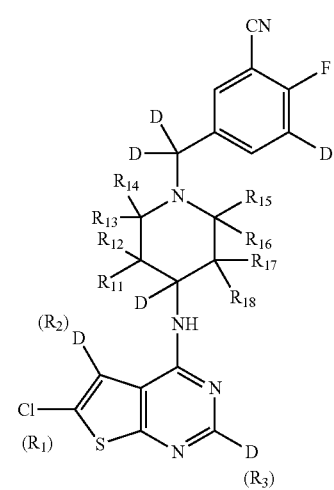
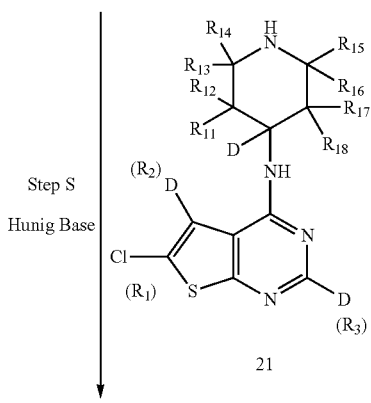

-continued

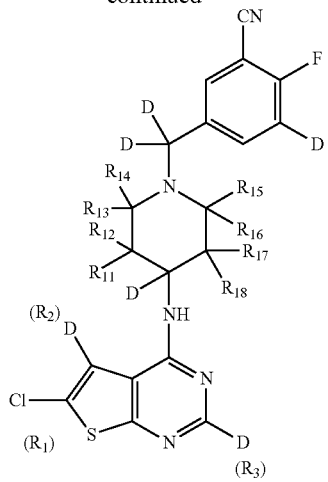

34

Methyl 3-cyano-4-fluorobenzoate 27 (1.8 g) is deuterated by heating with 1 equiv of $D_2O$ and conc. HCl at 180 degree C. under microwave irradiation for 30 minutes (Martin A.; Lautens M., Org. Lett. 2008, 10, 4351-4353). The reaction mixture is basified with aqueous solution of $NaHCO_3$ and extracted with ether. The combined ethereal extracts are concentrated, dried, filtered to and concentrated in vacuo. The concentrated oil is flash chromatogarphed to afford the mono-deuterated 28 (1.62 g).

28 is converted to aldehyde 29 by reducing with diisobutyl aluminum hydride (DIBALH) or diisobutyl aluminum deuteride (DIBALD) in toluene and converted to 31 by treating 28 with DIBALD in toluene at –78 C.

Step M: To a toluene solution of deuterated ester 28 (0.8 g) cooled to –78 C by placing the reaction flask in dry ice-acetone mixture, is added 1.1 equiv of DIBALH or DIBALD and the mixture stirred for 1 hour and quenched methanol and sodium hydroxide. The aqueous phase is extracted with solvent mixture of ether and ethyl acetate, dried extracts over $MgSO_4$, filtered and concentrated in vacuo to an oil which after flash column chromatography gave 29 (0.53 g).

Step N: To a solution of deuterated ester 28 (0.8 g) in toluene cooled to –78 C is added 1.1 equiv of DIBALD and the mixture stirred for 1 hour. Methanolic sodium hydroxide is added to reaction mixture and the aqueous phase is extracted with solvent mixture of ether and ethyl acetate, dried extracts over $MgSO_4$, filtered and concentrated in vacuo to an oil which after flash column chromatography gave 31 (0.55 g).

Step O: To a solution of deuterated ester 28 (0.8 g) in ether cooled to –78 C is added 1.1 equiv of $LiAlD_4$ and the mixture stirred for 1 hour. Aqueous NaOH is added to reaction mixture and stirred for 30 min and then the aqueous phase is extracted with ether and ethyl acetate, dried extracts over $MgSO_4$, filtered and concentrated in vacuo to an oil which after flash column chromatography gave 30 (0.5 g).

Step P: To a solution of 29 (0.5 g) in THF cooled to –78 C is added 1.2 equiv of $NaBD_4$ and the mixture stirred for 1 hour. Methanolic sodium hydroxide is added to reaction mixture and the aqueous phase is extracted with ether and ethyl acetate, dried extracts over anhydrous $MgSO_4$, filtered and concentrated in vacuo to an oil which after flash column chromatography afforded 30 (0.36 g).

Step Q: To a solution of 30 (0.86 g) in dichloromethane at 0 degree is added carbon tetrabromide (1.1 equiv) and stirred. After 5 min, triphenyl phosphine (1 equiv) is added and the resulting mixture stirred for 1 h at 0 degree and allowed to warm to room temperature. The mixture treated with methanol and the mixture concentrated in vacuo, then purification by flash column chromatography gave the tri-deuterated aryl bromide 32 (0.66 g).

The substituted deuterated benzyl bromide 30 can also be converted to the corresponding deuterated aldehyde 31 by its oxidation with PDC (pyridinium dichromate) in methylene chloride in the presence of dry molecular sieves.

Step R: To a mixture of 21 (0.3 g) and deuterated aldehyde 29 is added DCE and $NaBD(OAc)_3$ (1.5 equiv) and deuterated acetic acid-$d_4$ (2 equiv). The reaction mixture is stirred for 12 h at room temperature before the addition of aqueous $NaHCO_3$ solution. The product is extracted with ethyl acetate, dried over anhydrous $MgSO_4$, filtered and concentrated in vacuo to give an oil which is then purified by flash column chromatography to yield the final compound 33 (0.36 g).

The compound 34 is prepared from the aldehyde 31 by using the procedure described in step R.

Step S: To a solution of 21 (0.28 g) and 0.4 ml of di-isopropylethylamine (Hunigs base) in 3 ml of $CH_3$ CN is added 32 and the resulting mixture was heated at 85° C. with stirring for 12 h. The mixture is cooled to room temperature and poured over to aqueous sodium bicarbonate solution. The mixture is extracted with ethyl acetate and the combined organic extracts are dried over sodium sulfate, filtered and concentrated in vacuo. The residue is purified by flash column chromatography to give 34 (0.3 g).

To prepare the fully deuterated (or per-deuterated) aldehyde or bromide analogs of 29, 31 and 32, the fully deuterated precursor 38 is prepared from the corresponding aniline 35 as illustrated in Scheme 9 below.

Step T: Methyl 3-amino-4-fluorobenzoate 35 (1.7 g) is heated with 1 equiv of conc HCl and $D_2O$ at 180° C. under microwave irradiation for 30 minutes. The mixture is cooled to room temperature and treated with methanol and basified with aqueous solution of $NaHCO_3$. The mixture is extracted with ether/ethyl acetate mixture, washed combined organic extracts with brine, dried over sodium sulfate, filtered and concentrated in vacuo. The crude product is purified by flash column chromatography to yield di-deuterated aniline 36 (1.3 g).

Step U: The deuterated aniline 36 (1.3 g) is diazotized by treating it with sodium nitrite (1.1 equiv) in the presence of sulfuric acid at 0° C. for 6 hours. The diazonium salt intermediate is treated with potassium cyanide (1 equiv) at 0° C. to room temperature for 6 hours. Aqueous NaHCO₃ solution is added to the reaction mixture slowly and then extracted with solvent mixture of ether/ethyl acetate. The combined extracts are dried over anhydrous sodium sulfate, filtered and concentrated in vacuo. The product is isolated by purification of the residue by flash column chromatography to afford the nitrile 37 (0.9 g).

Using the microwave irradiation method as described in step T, 37 (0.9 g) is converted into 38 (0.65 g) by substituting deuterium ortho to fluorine substituent at the benzene ring of 38.

38 is then converted to the corresponding aldehydes and bromide as described for 27 in Scheme 8 to couple with 21 to produce the deuterated derivatives of pyrimidines 33 and 34.

All compounds of formula I containing deuterated N-D group is prepared from the corresponding N—H containing precursor by treating N—H precursor with deuterated methanol-$d_1$ (CH₃OD) or methanol-$d_4$ (CD₃OD) or deuterated acetic acid-$d_4$ (CD₃CO₂D).

The pharmaceutical salts including maleate, fumarate, acetate, mesylate, tartarate, citrate, HCl, etc., are prepared by treatment of the free bases e.g., 33 and 34 with appropriate acids in a suitable solvent such as ether. methanol, or methylene chloride, etc. followed by removal of the solvent in vacuo.

Scheme 9:

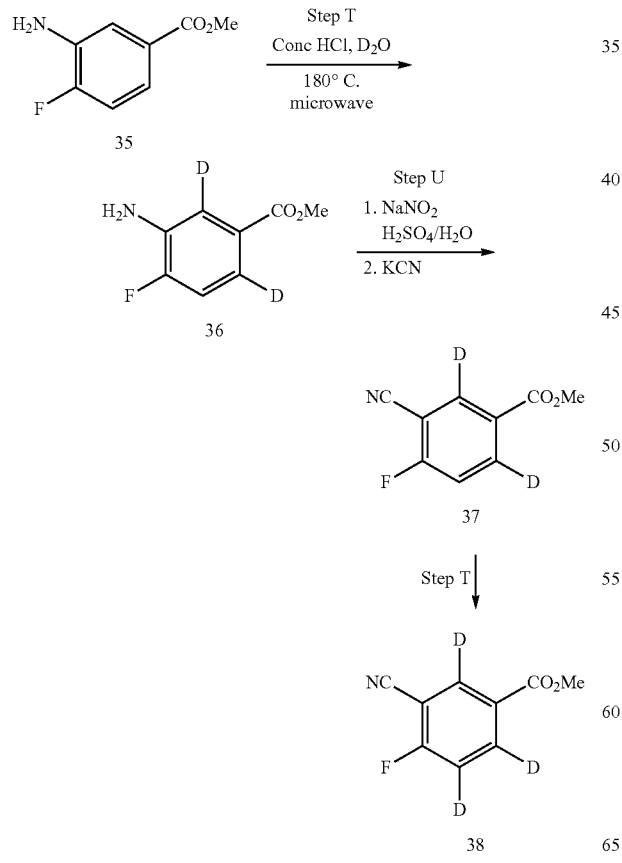

EXAMPLES

Given below are compounds that are representative examples of the present invention.

Example 1

N-(1-(3-Cyano-4-fluorobenzyl-$d_2$)piperidin-4-yl-$d_5$)-6-chlorothieno-$d_1$[2,3-d]pyrimidine-4-amine-$d_1$

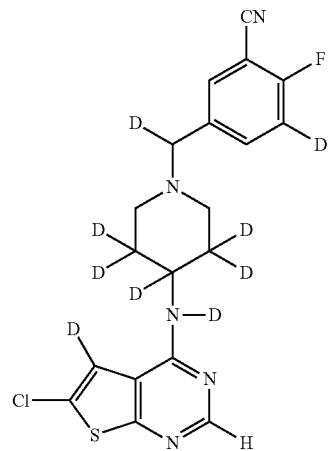

The title compound is prepared by using the methods described in scheme above. Mass spectral analysis (m/e): 411 (M+1).

Example 2

N-(1-(3-Cyano-4-fluorobenzyl-$d_4$)piperidin-4-yl-$d_5$)-6-chlorothieno-$d_1$[2,3-d]pyrimidine-4-amine-$d_1$

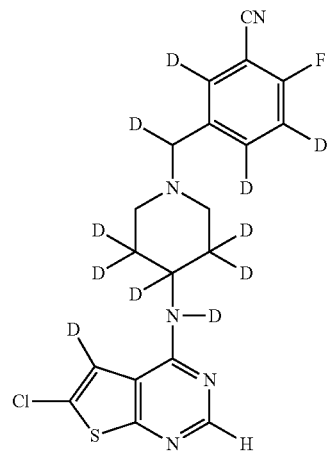

The title compound is prepared by using the methods described in scheme above. MS (m/e): 413 (M+1).

Example 3

N-(1-(3-Cyano-4-fluorobenzyl-$d_5$)piperidin-4-yl-$d_5$)-6-chlorothieno-$d_1$[2,3-d]pyrimidine-4-amine-$d_1$

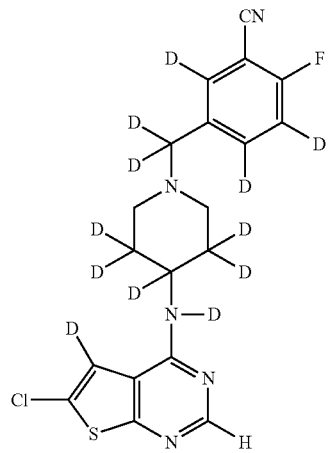

The title compound is prepared by using the methods described in scheme above. MS (m/e): 414 (M+1).

Example 4

N-(1-(3-Cyano-4-fluorobenzyl-$d_5$)piperidin-4-yl-$d_5$)-6-chlorothieno-$d_1$[2,3-d]pyrimidine-$d_1$-4-amine-$d_1$

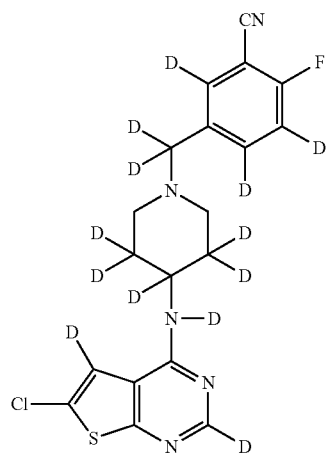

The title compound is prepared by using the methods described in schemes above. MS (m/e): 415 (M+1).

Example 5

N-(1-(3-Cyano-4-fluorobenzyl-$d_2$)piperidin-4-yl-$d_5$)-6-chlorothieno-$d_1$[3,2-d]pyrimidine-4-amine-$d_1$

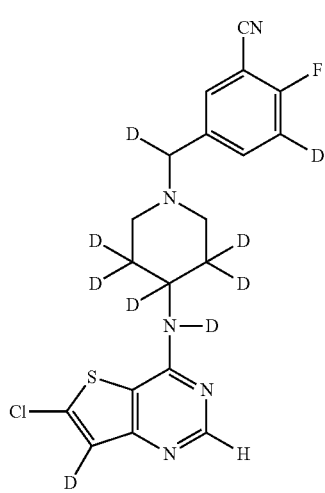

The title compound is prepared by using the methods described in scheme above. Mass spectral analysis (m/e): 411 (M+1).

Example 6

N-(1-(3-Cyano-4-fluorobenzyl-$d_4$)piperidin-4-yl-$d_5$)-6-chlorothieno-$d_1$[3,2-d]pyrimidine-4-amine-$d_1$

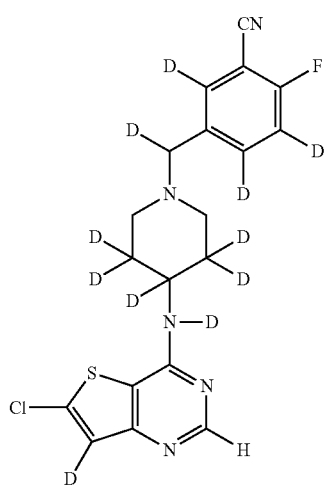

The title compound is prepared by using the methods described in scheme above. MS (m/e): 413 (M+1).

Example 7

N-(1-(3-Cyano-4-fluorobenzyl-d5)piperidin-4-yl-d5)-6-chlorothieno-d1[3,2-d]pyrimidine-4-amine-d1

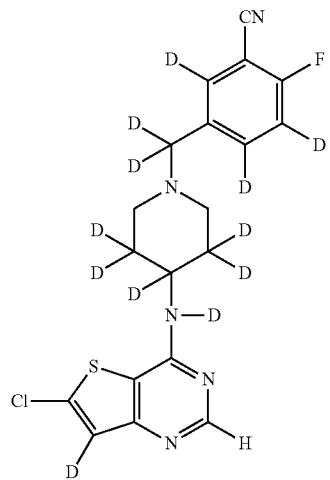

The title compound is prepared by using the methods described in scheme above. MS (m/e): 414 (M+1).

Example 8

N-(1-(3-Cyano-4-fluorobenzyl-d5)piperidin-4-yl-d5)-6-chlorothieno-d1[3,2-d]pyrimidine-d1-4-amine-d1.

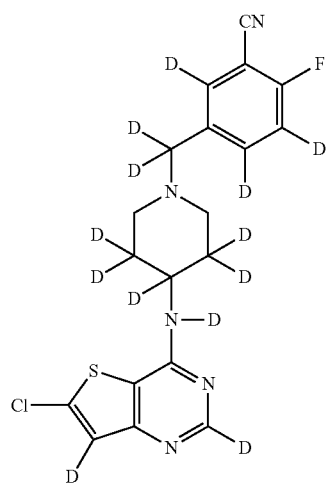

The title compound is prepared by using the methods described in scheme above. MS (m/e): 415 (M+1).

Example 9

N-(1-(3-Cyano-4-fluorobenzyl-d2)piperidin-4-yl-d5)-2-chlorothiazolo[5,4-d]pyrimidine-7-amine-d1

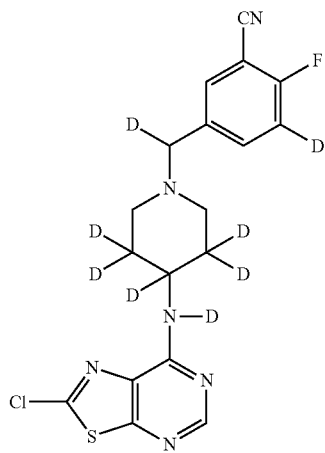

The title compound is prepared by using the methods as described in scheme above and appropriate modifications thereof. MS (m/e): 411 (M+1).

Example 10

N-(1-(3-Cyano-4-fluorobenzyl-d4)piperidin-4-yl-d5)-2-chlorothiazolo[5,4-d]pyrimidine-7-amine-d1

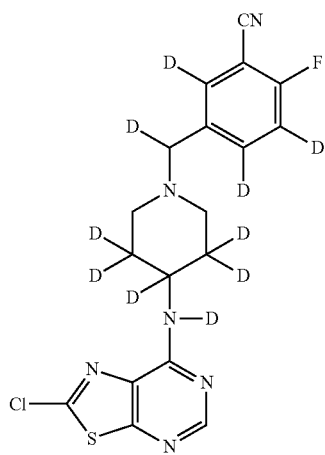

The title compound is prepared by using the methods described in scheme above and appropriate modifications thereof. MS (m/e): 413 (M+1).

Example 11

N-(1-(3-Cyano-4-fluorobenzyl-d$_5$)piperidin-4-yl-d$_5$)-2-chlorothiazolo[5,4-d]pyrimidine-7-amine-d$_1$

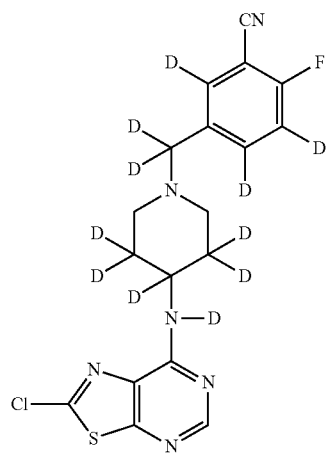

The title compound is prepared by using the methods described in scheme above and appropriate modifications thereof. MS (m/e): 414 (M+1).

Example 12

N-(1-(3-Cyano-4-fluorobenzyl-d$_5$)piperidin-4-yl-d$_5$)-2-chlorothiazolo[5,4-d]pyrimidine-5-d$_1$-7-amine-d$_1$

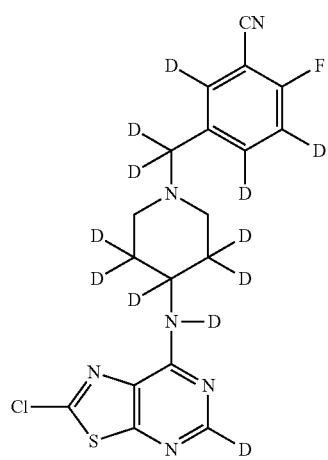

The title compound is prepared by using the methods described in scheme above and appropriate modifications thereof. MS (m/e): 415 (M+1).

Example 13

N-(1-(3-Cyano-4-fluorobenzyl-d$_2$)piperidin-4-yl-d$_5$)-2-chlorothiazolo[4,5-d]pyrimidine-7-amine-d$_1$

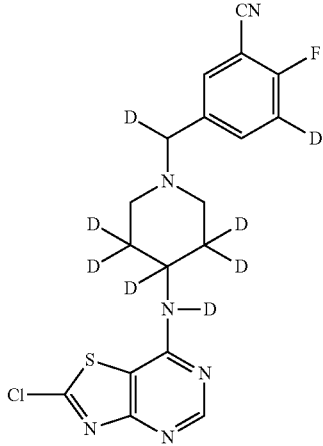

The title compound is prepared by using the methods described in scheme above and appropriate modifications thereof. MS (m/e): 411 (M+1).

Example 14

N-(1-(3-Cyano-4-fluorobenzyl-d$_4$)piperidin-4-yl-d$_5$)-2-chlorothiazolo[4,5-d]pyrimidine-7-amine-d$_1$

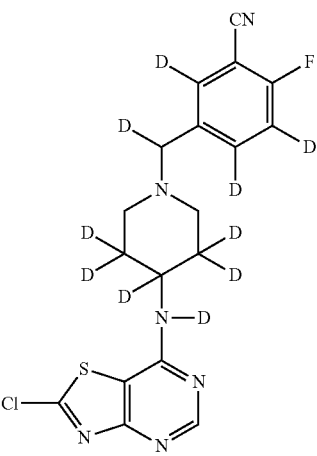

The title compound is prepared by using the methods described in scheme above and appropriate modifications thereof. MS (m/e): 413 (M+1).

Example 15

N-(1-(3-Cyano-4-fluorobenzyl-d₅)piperidin-4-yl-d₅)-
2-chlorothiazolo[4,5-d]pyrimidine-7-amine-d₁

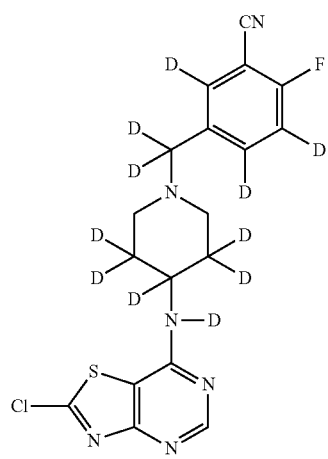

The title compound is prepared by using the methods described in scheme above and appropriate modifications thereof. MS (m/e): 414 (M+1).

Example 16

N-(1-(3-Cyano-4-fluorobenzyl-d₅)piperidin-4-yl-d₅)-
2-chlorothiazolo[4,5-d]pyrimidine-5-d₁-7-amine-d₁

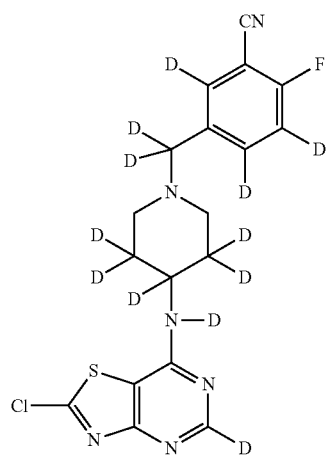

The title compound is prepared by using the methods described in scheme above and appropriate modifications thereof. MS (m/e): 415 (M+1).

Example 17

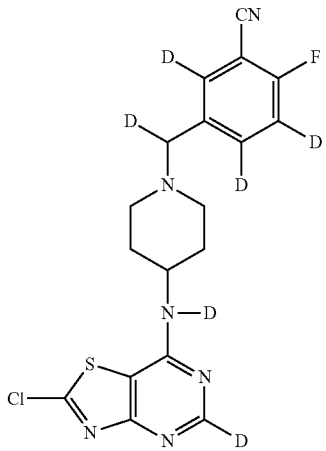

The title compound is prepared by using the methods described in scheme above and appropriate modifications thereof. MS (m/e): 409 (M+1).

Example 18

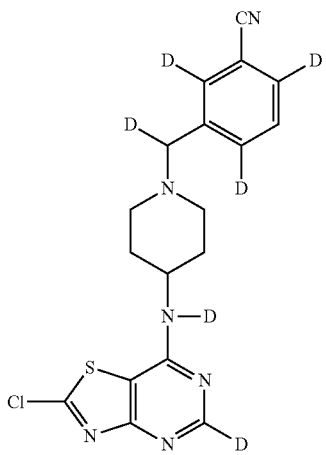

This compound is prepared by using the methods described in scheme above and appropriate modifications thereof. MS (m/e): 391 (M+1).

Example 19

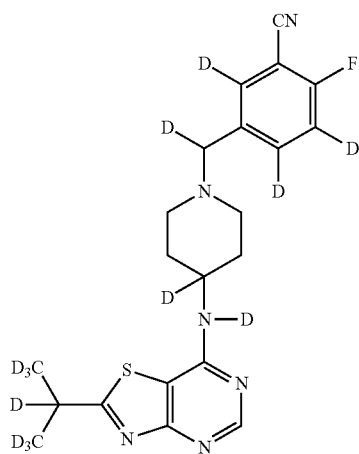

This compound is prepared by using the methods described in scheme above and appropriate modifications thereof. MS (m/e): 424 (M+1).

Example 20

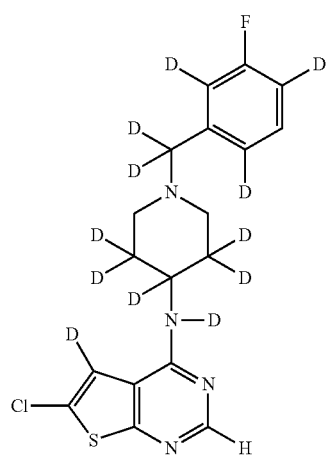

This compound is prepared by using the methods described in scheme above and appropriate modifications thereof. MS (m/e): 389 (M+1).

Example 21

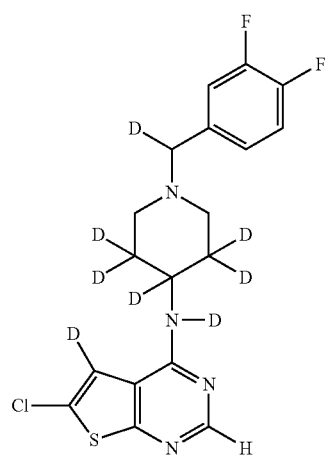

This compound is prepared by using the methods described in scheme above and appropriate modifications thereof. MS (m/e): 403 (M+1).

Example 22

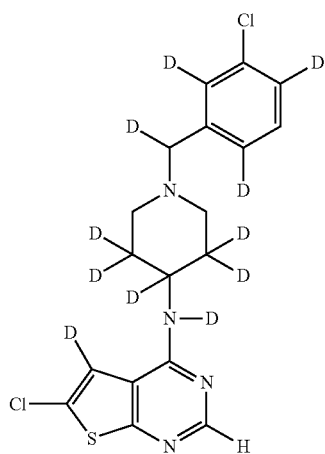

This compound is prepared by using the methods described in scheme above and appropriate modifications thereof. MS (m/e): 404 (M+1).

Example 23

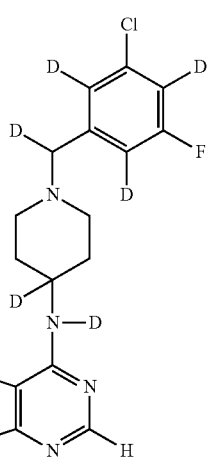

This compound is prepared by using the methods described in scheme above and appropriate modifications thereof. MS (m/e): 418 (M+1).

Example 24

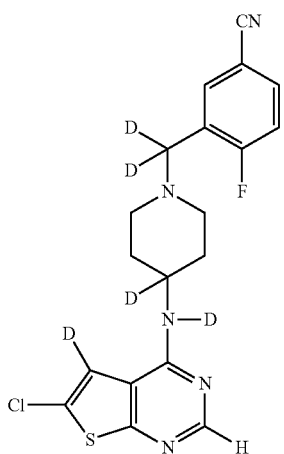

This compound is prepared by using the methods described in scheme above and appropriate modifications thereof. MS (m/e): 407 (M+1).

Example 25

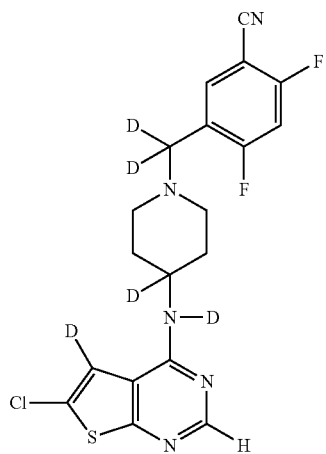

This compound is prepared by using the methods described in scheme above and appropriate modifications thereof. MS (m/e): 425 (M+1).

Example 26

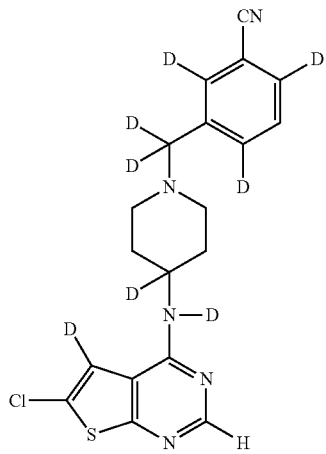

This compound is prepared by using the methods described in scheme above and appropriate modifications thereof. MS (m/e): 392 (M+1).

Example 27

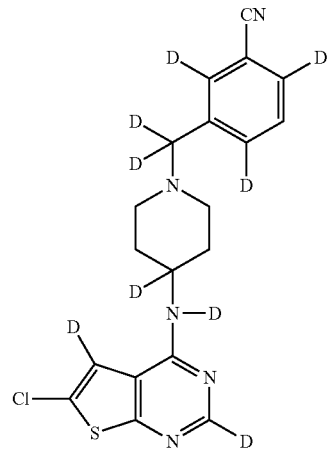

This compound is prepared by using the methods described in scheme above and appropriate modifications thereof. MS (m/e): 393 (M+1).

Example 28

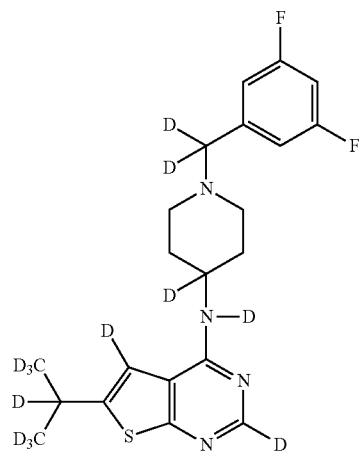

This compound is prepared by using the methods described in scheme above and appropriate modifications thereof. MS (m/e): 416 (M+1).

Example 29

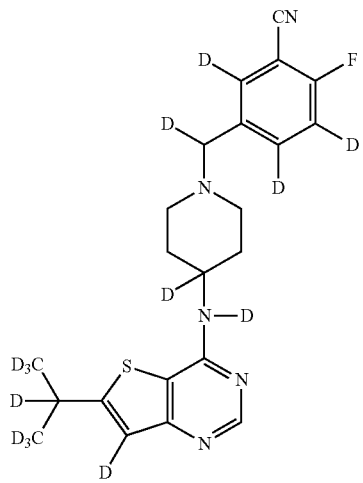

This compound is prepared by using the methods described in scheme above and modifications thereof. MS (m/e): 424 (M+1).

Example 30

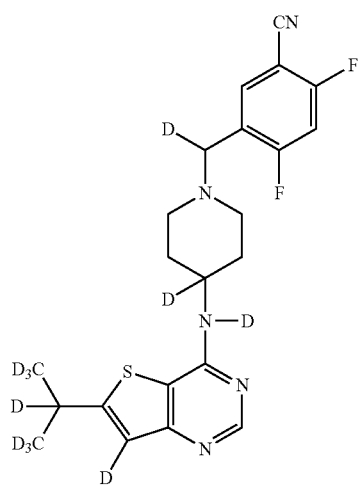

This compound is prepared by using the methods described in scheme above and modifications thereof. MS (m/e): 439 (M+1).

Example 31

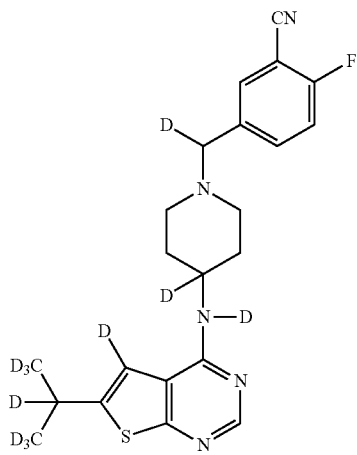

This compound is prepared by using the methods described in scheme above and modifications thereof. MS (m/e): 421 (M+1).

Example 32

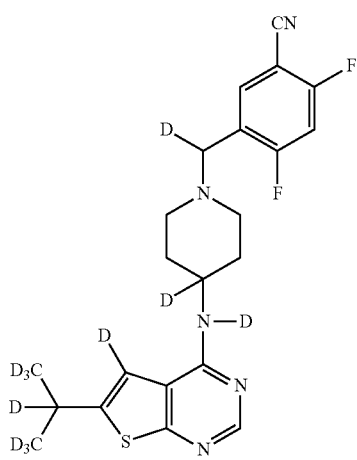

This compound is prepared by using the methods described in scheme above and modifications thereof. MS (m/e): 438 (M+1).

Example 33

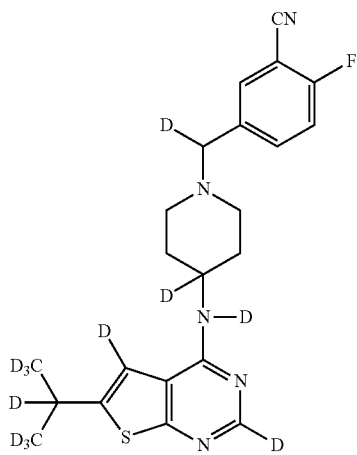

This compound is prepared by using the methods described in scheme above and modifications thereof. MS (m/e): 422 (M+1).

Example 34

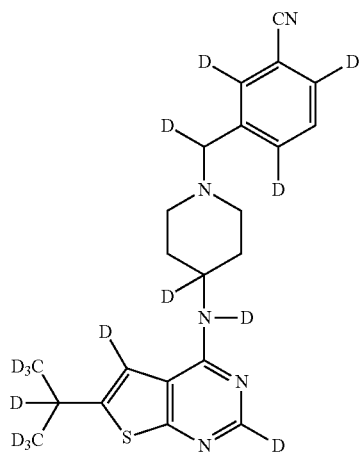

This compound is prepared by using the methods described in scheme above and modifications thereof. MS (m/e): 407 (M+1).

Example 35

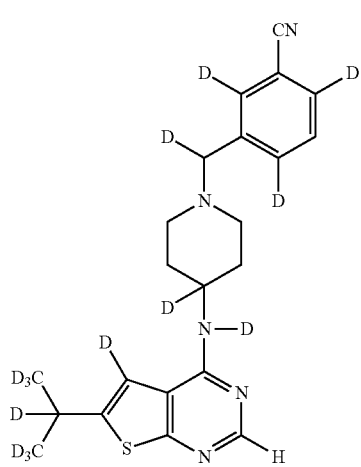

This compound is prepared by using the methods described in scheme above and modifications thereof. MS (m/e): 406 (M+1).

Example 36

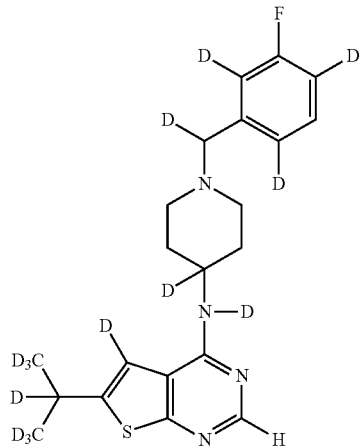

This compound is prepared by using the methods described in scheme above and modifications thereof. MS (m/e): 399 (M+1).

Example 37

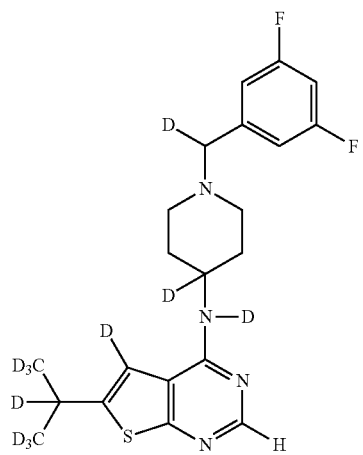

This compound is prepared by using the methods described in scheme above and modifications thereof. MS (m/e): 414 (M+1).

Example 38

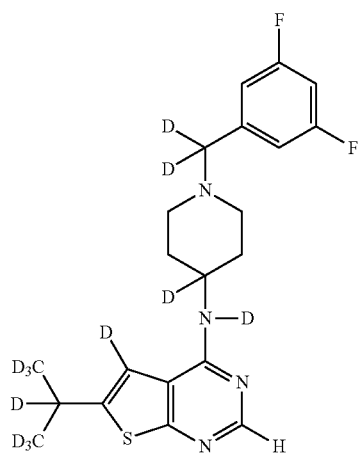

This compound is prepared by using the methods described in scheme above and modifications thereof. MS (m/e): 415 (M+1).

Example 39

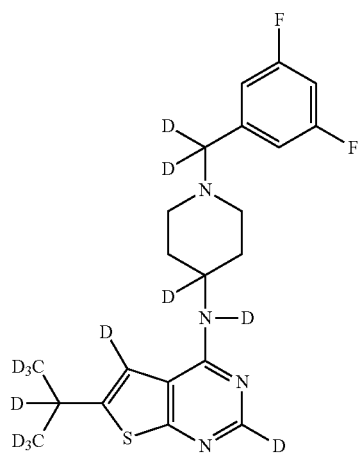

This compound is prepared by using the methods described in scheme above and modifications thereof. MS (m/e): 416 (M+1).

Example 40

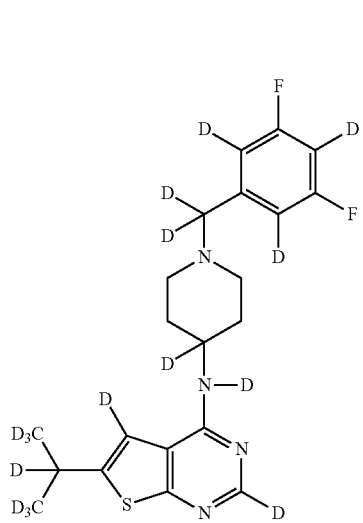

This compound is prepared by using the methods described in scheme above and modifications thereof. MS (m/e): 419 (M+1).

Example 41

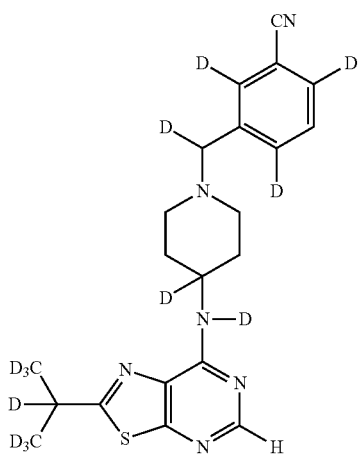

This compound is prepared by using the methods described in scheme above and modifications thereof. MS (m/e): 406 (M+1).

Example 42

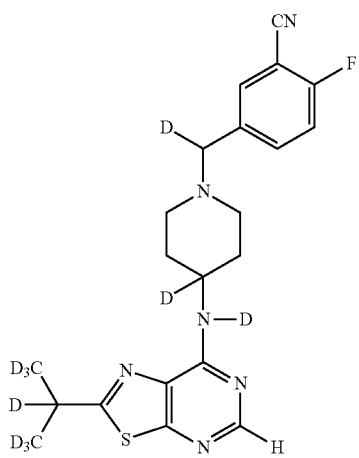

This compound is prepared by using the methods described in scheme above and modifications thereof. MS (m/e): 421 (M+1).

Example 43

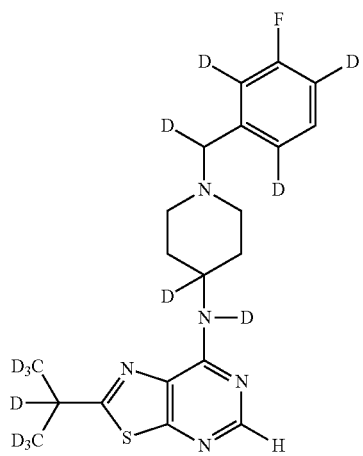

This compound is prepared by using the methods described in scheme above and modifications thereof. MS (m/e): 399 (M+1).

Example 44

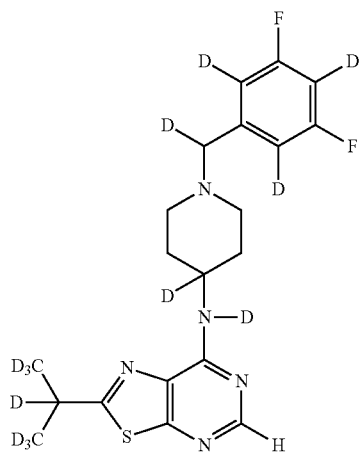

This compound is prepared by using the methods described in scheme above and modifications thereof. MS (m/e): 417 (M+1).

Example 45

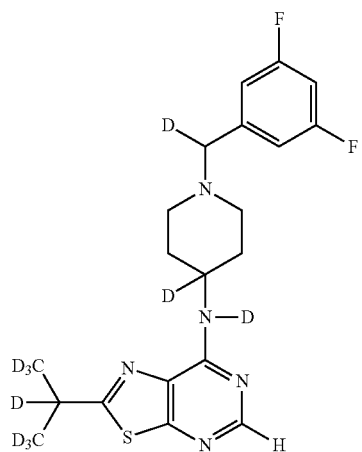

This compound is prepared by using the methods described in scheme above and modifications thereof. MS (m/e): 414 (M+1).

Example 46

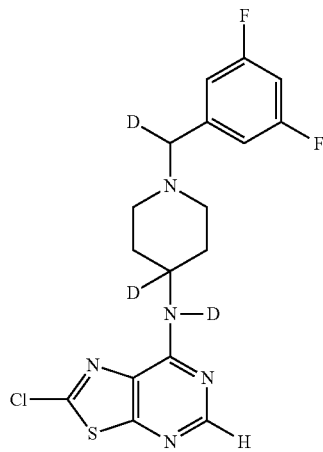

This compound is prepared by using the methods described in scheme above and modifications thereof. MS (m/e): 399 (M+1).

Example 47

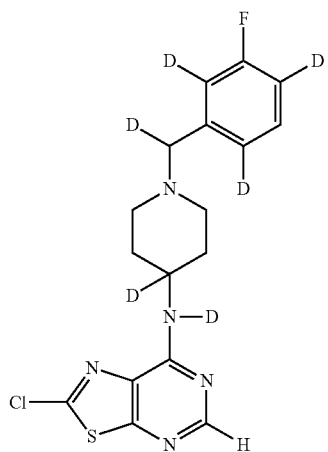

This compound is prepared by using the methods described in scheme above and modifications thereof. MS (m/e): 384 (M+1).

Example 48

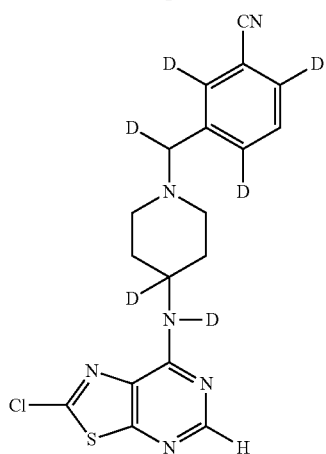

This compound is prepared by using the methods described in scheme above and modifications thereof. MS (m/e): 391 (M+1).

Example 49

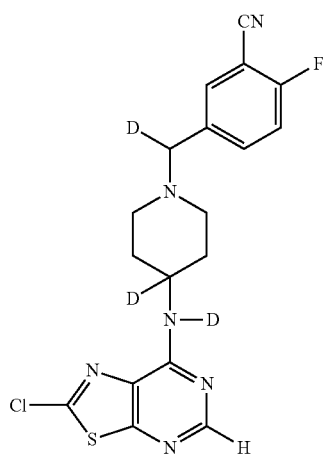

This compound is prepared by using the methods described in scheme above and modifications thereof. MS (m/e): 406 (M+1).

Example 50

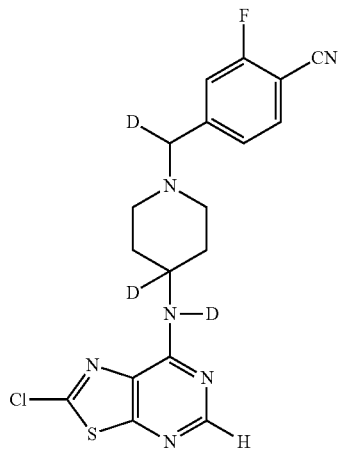

This compound is prepared by using the methods described in scheme above and modifications thereof. MS (m/e): 406 (M+1).

Example 51

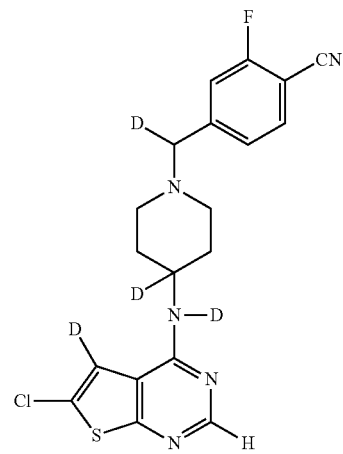

This compound is prepared by using the methods described in scheme above and modifications thereof. MS (m/e): 406 (M+1).

Example 52

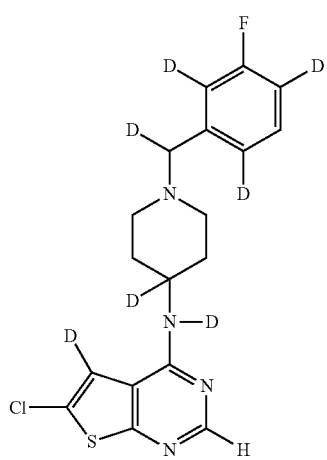

This compound is prepared by using the methods described in scheme above and modifications thereof. MS (m/e): 383 (M+1).

Example 53

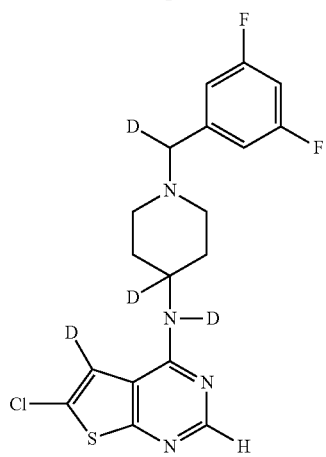

This compound is prepared by using the methods described in scheme above and modifications thereof. MS (m/e): 399 (M+1).

Example 54

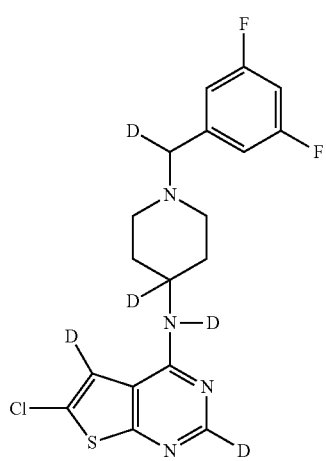

This compound is prepared by using the methods described in scheme above and modifications thereof. MS (m/e): 400 (M+1).

Example 55

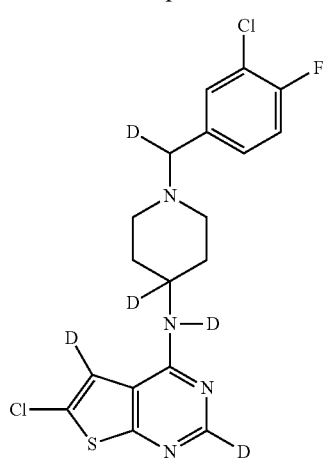

This compound is prepared by using the methods described in scheme above and modifications thereof. MS (m/e): 416 (M+1).

Example 56

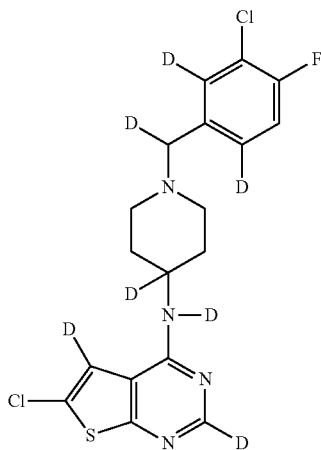

This compound is prepared by using the methods described in scheme above and modifications thereof. MS (m/e): 418 (M+1).

Example 57

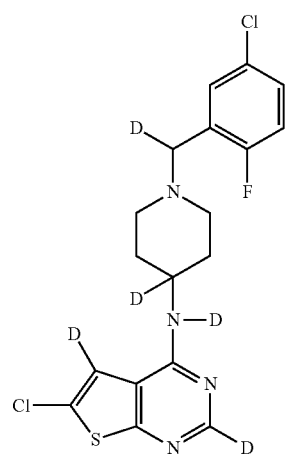

This compound is prepared by using the methods described in scheme above and modifications thereof. MS (m/e): 416 (M+1).

Example 58
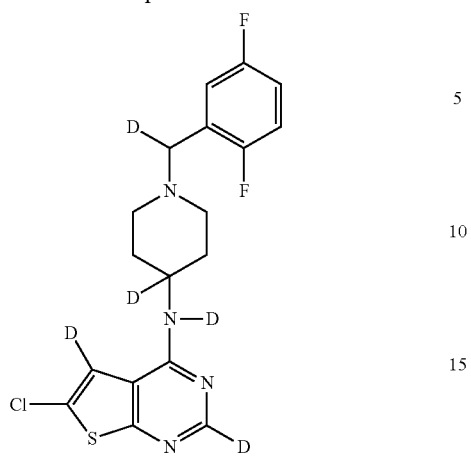
This compound is prepared by using the methods described in scheme above and modifications thereof. MS (m/e): 400 (M+1).
Example 59
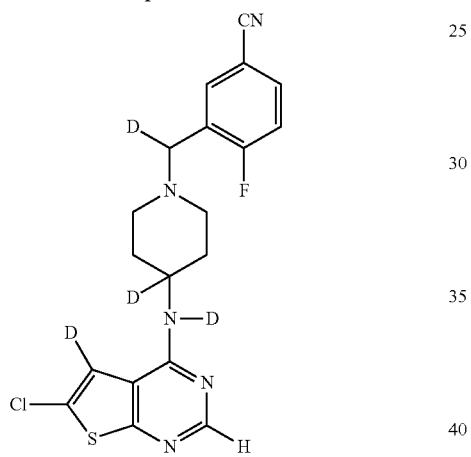
This compound is prepared by using the methods described in scheme above and modifications thereof. MS (m/e): 406 (M+1).
Example 60
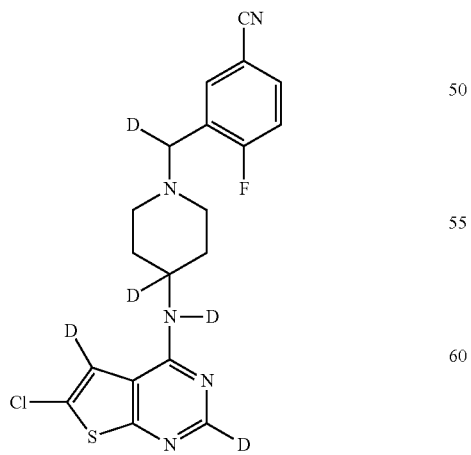
This compound is prepared by using the methods described in scheme above and modifications thereof. MS (m/e): 407 (M+1).
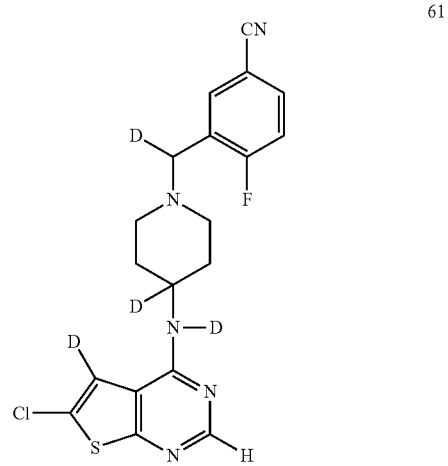
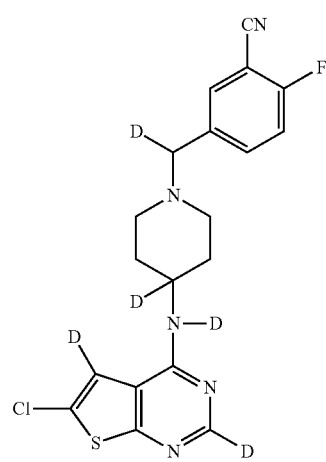
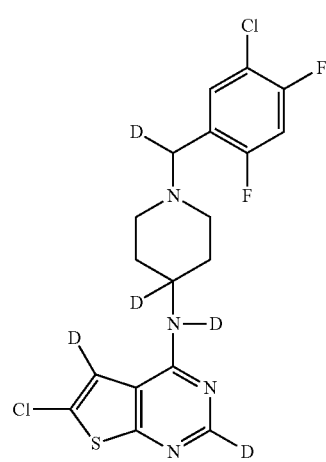

64
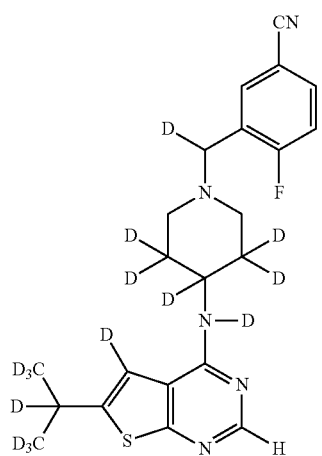
65
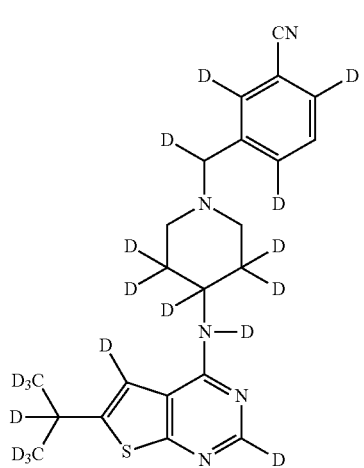
66
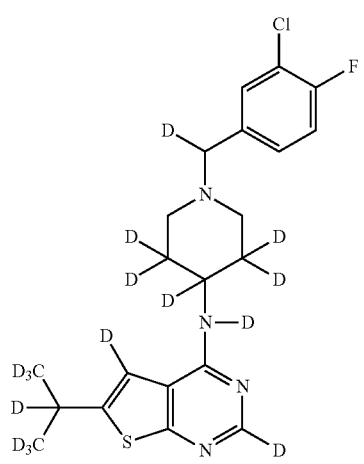
67
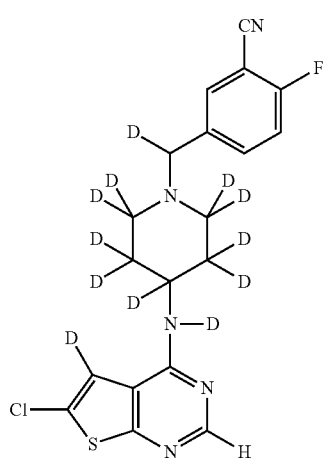
68
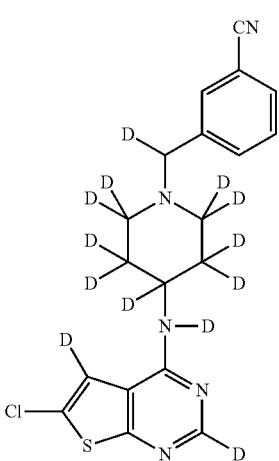
69
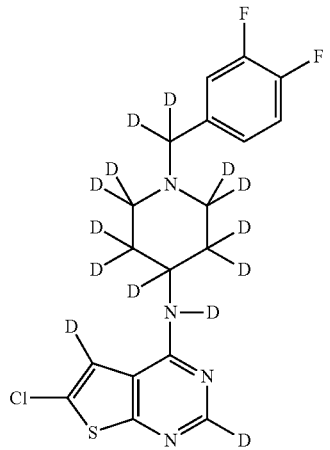

70 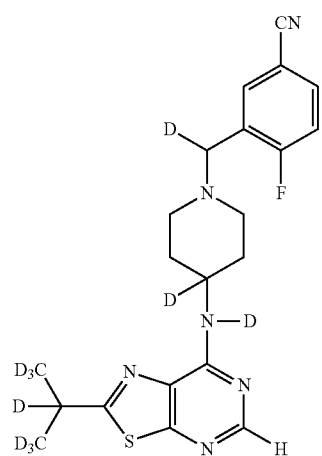
71 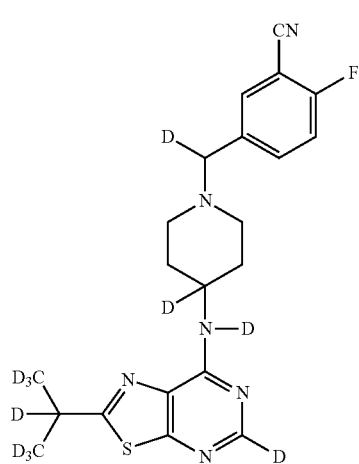
72 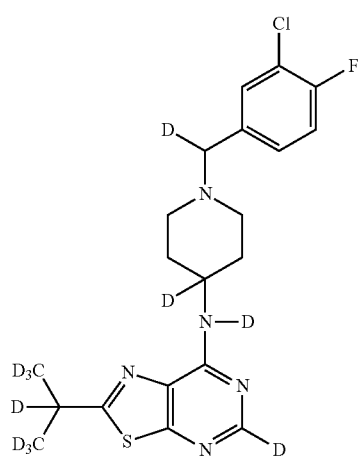
73 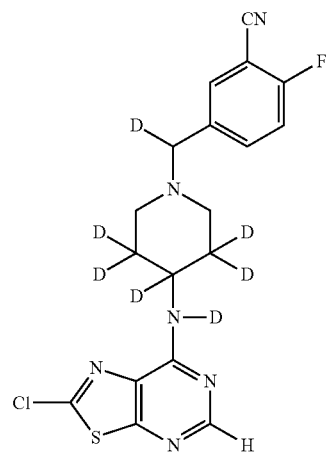
74 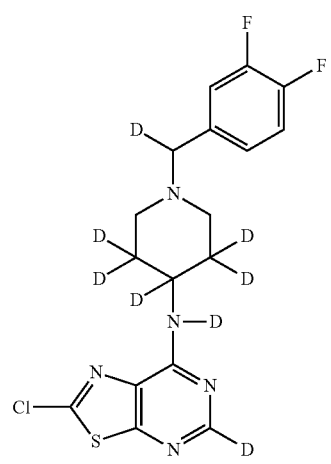
75 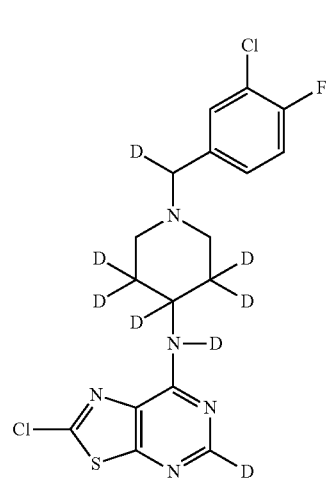

76
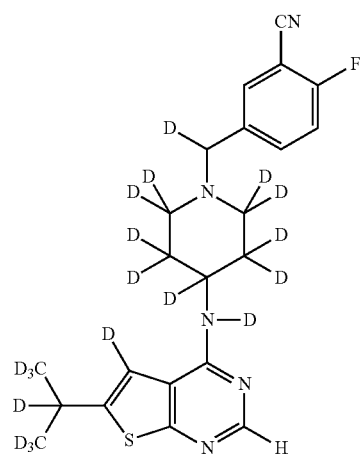
77
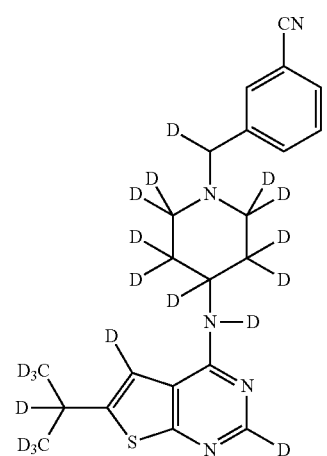
78
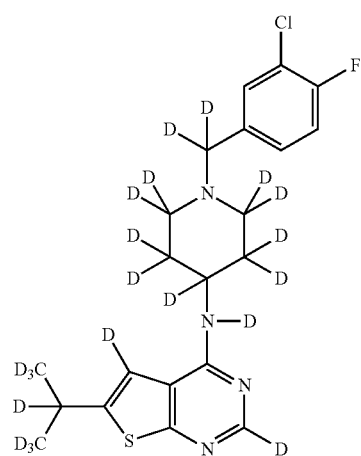
79
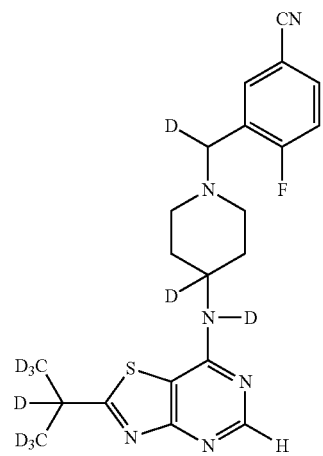
80
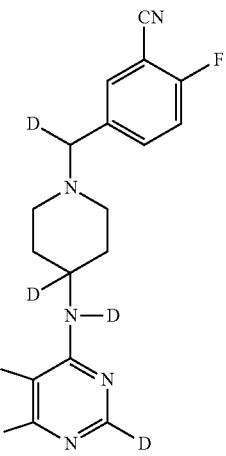
81
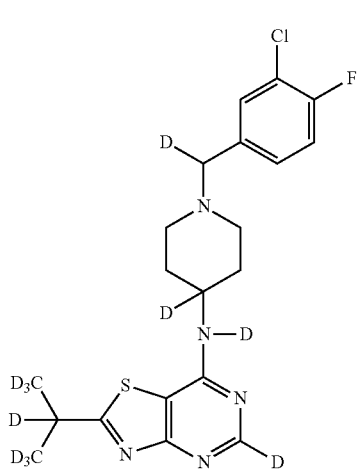

82
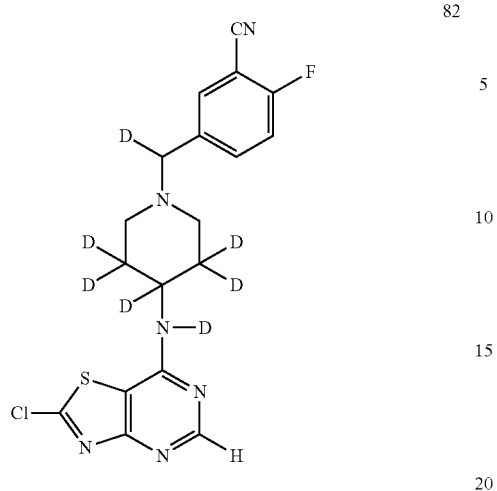
83
85
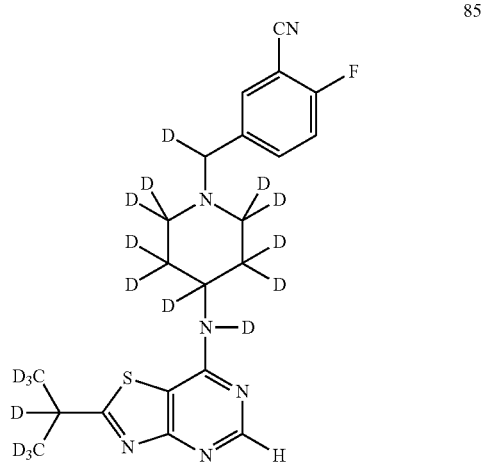
86
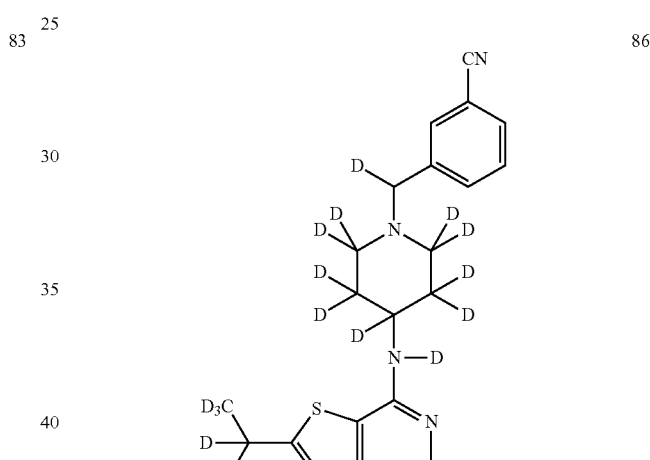
84
87
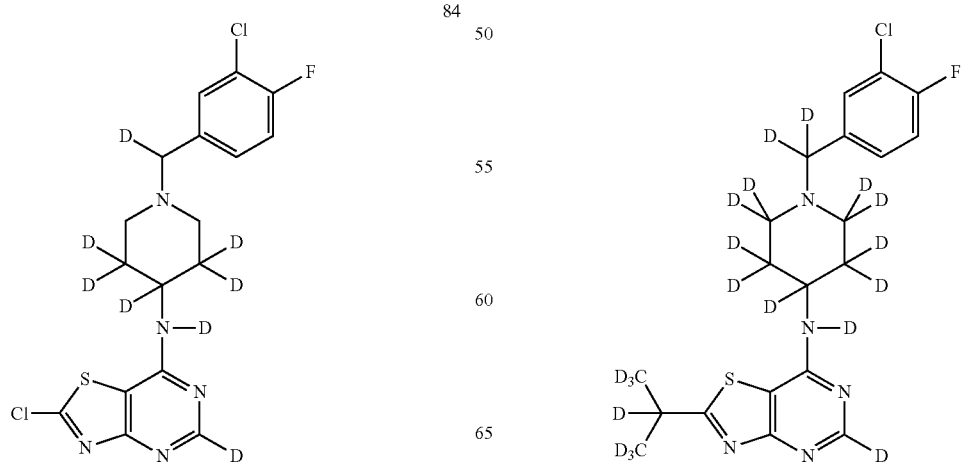

88
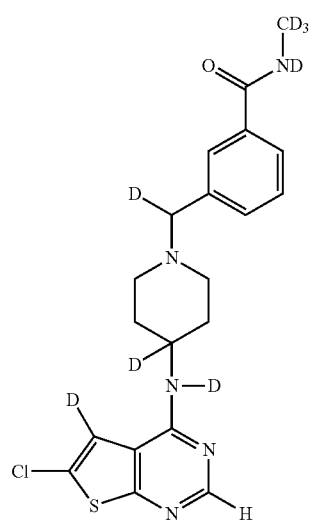
89
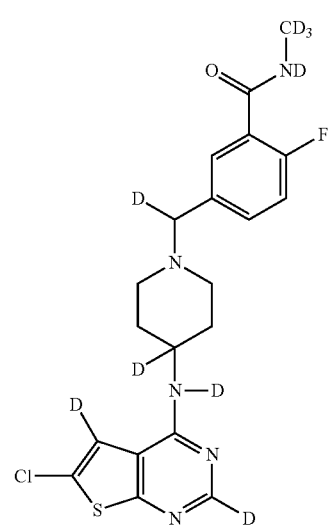
90
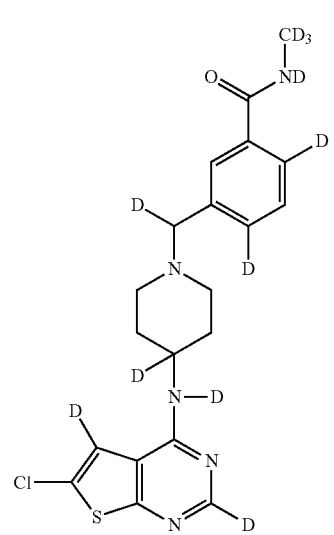
91
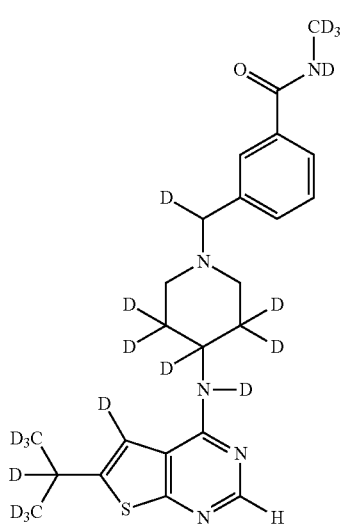
92
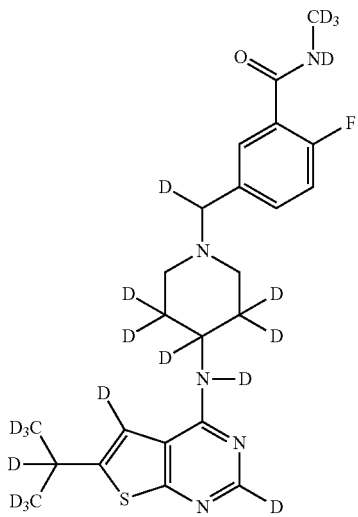
93
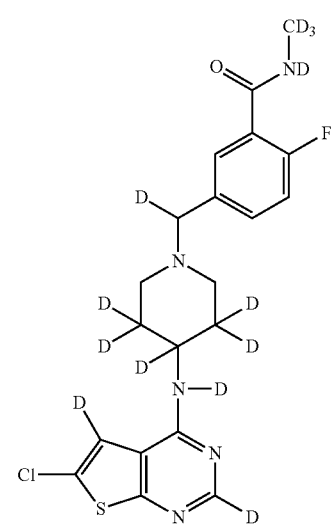

94
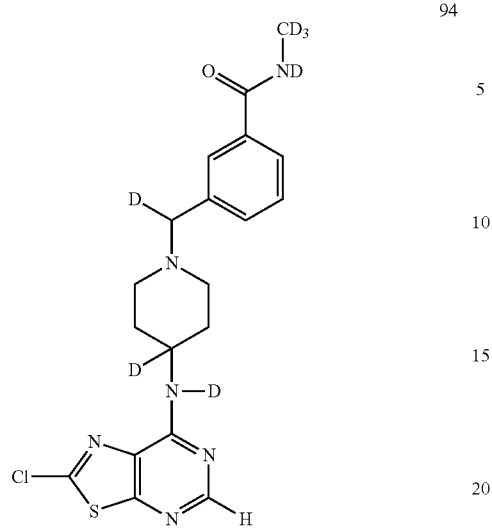
95
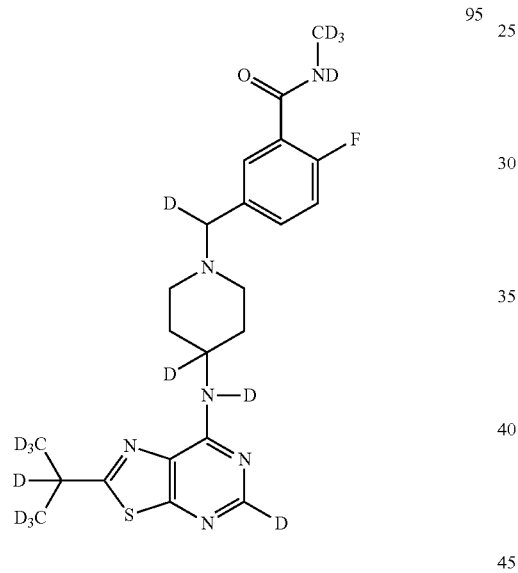
96
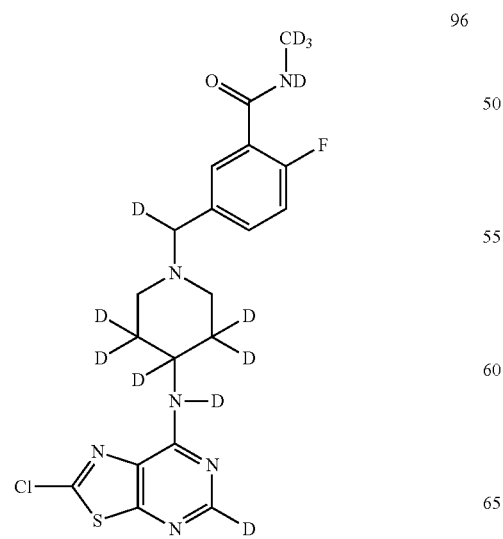
97
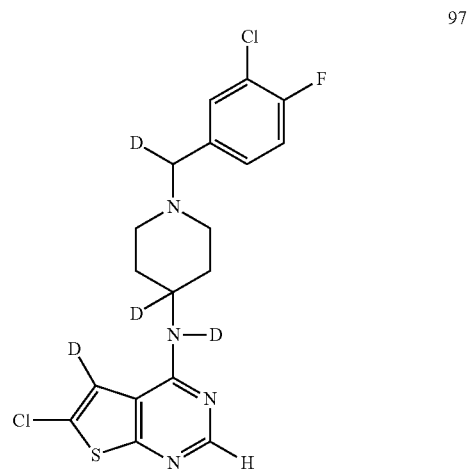
98
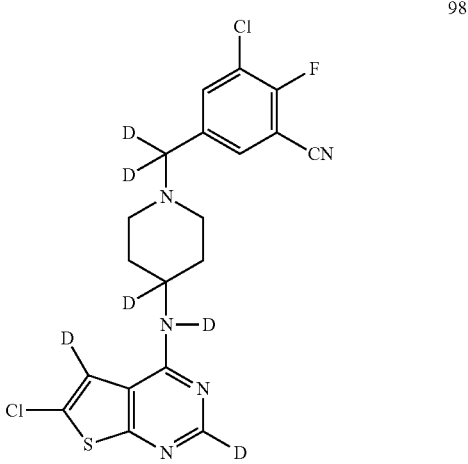
99
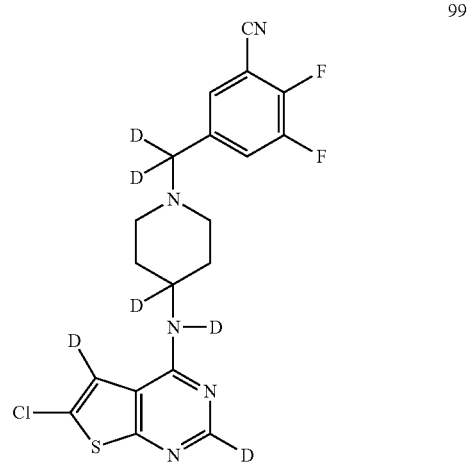

100 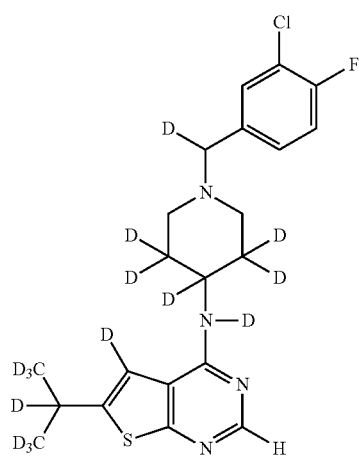
101 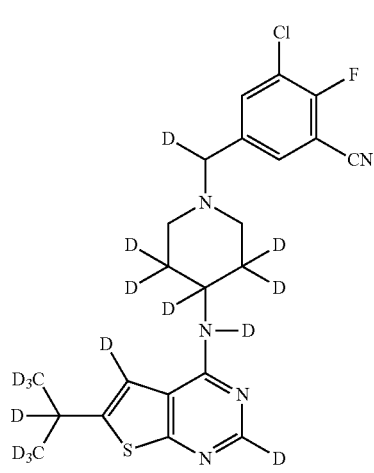
102 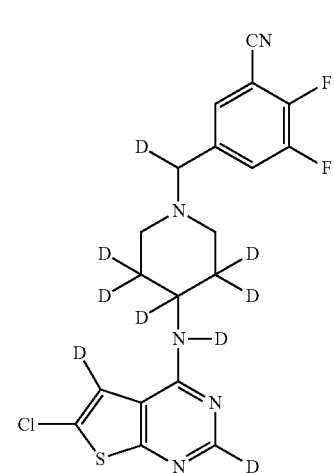
103 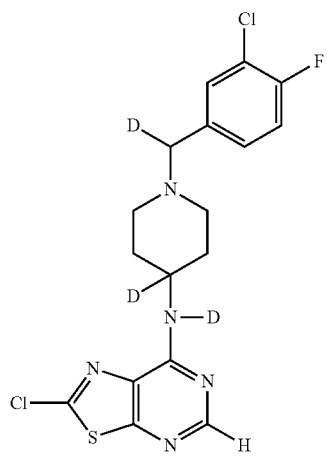
104 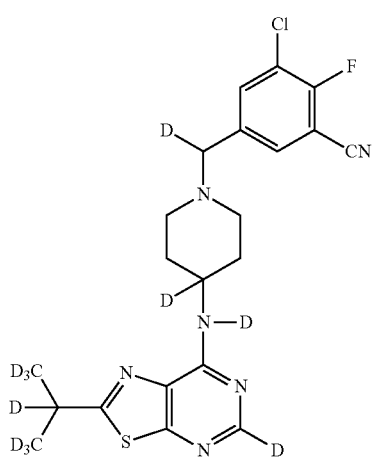
105 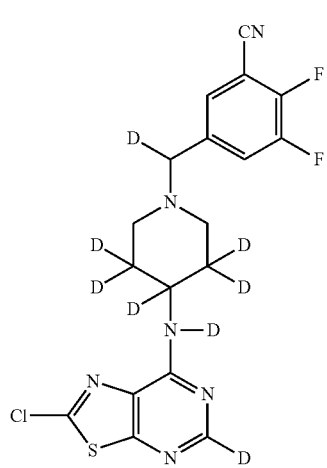

106
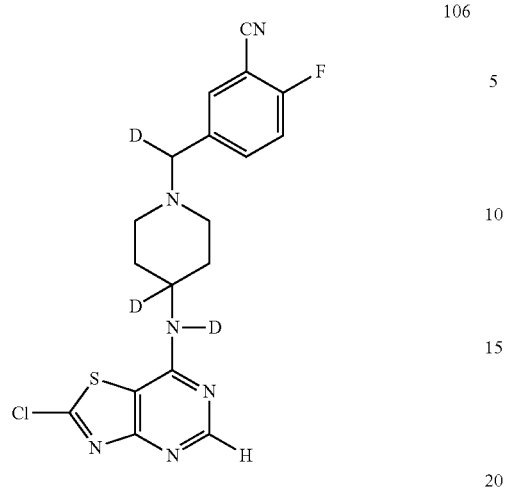
107
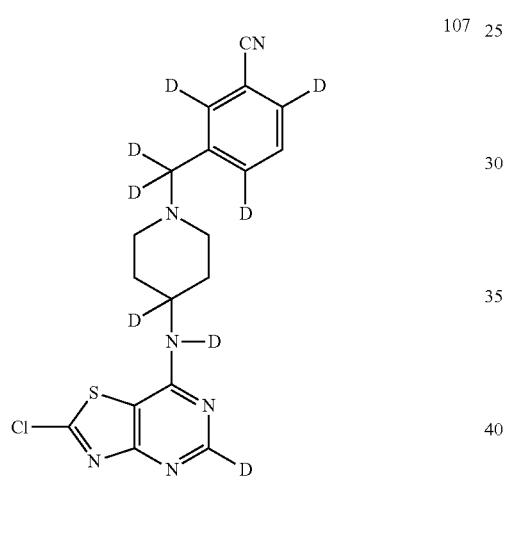
108
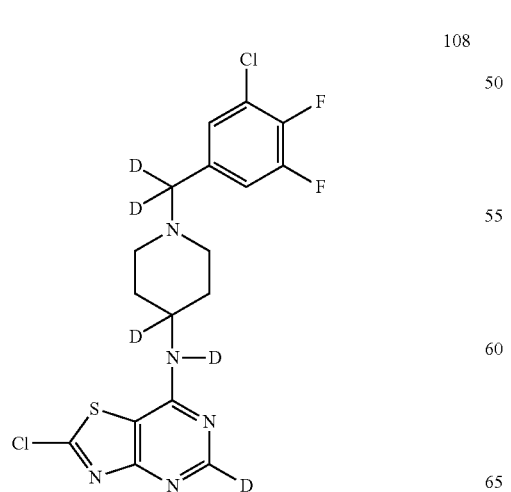
109
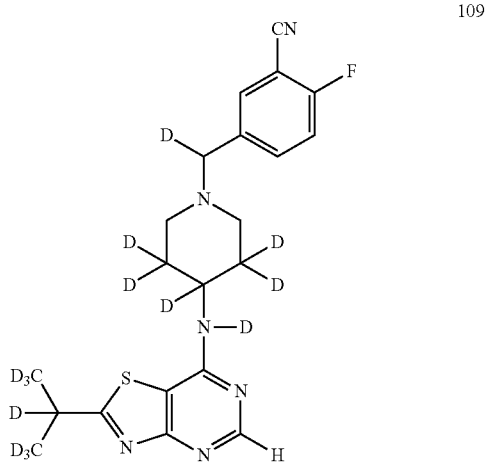
110
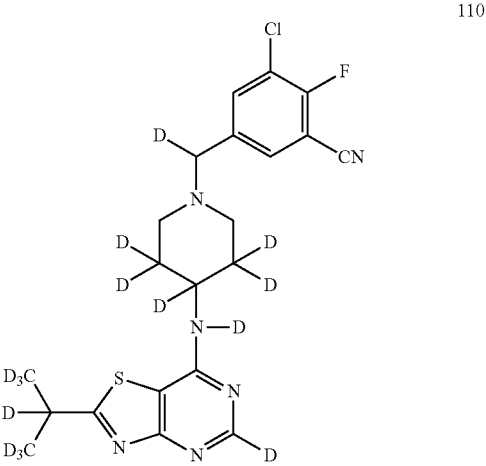
111
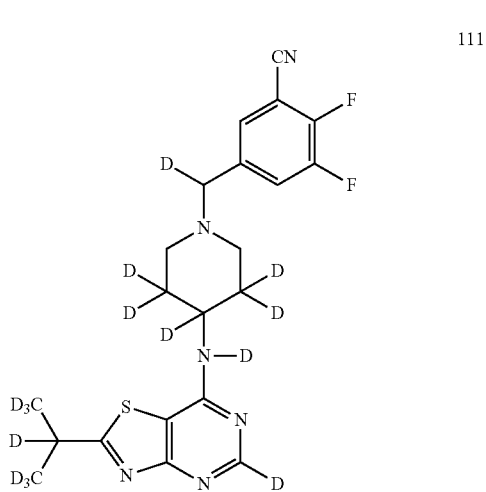

112

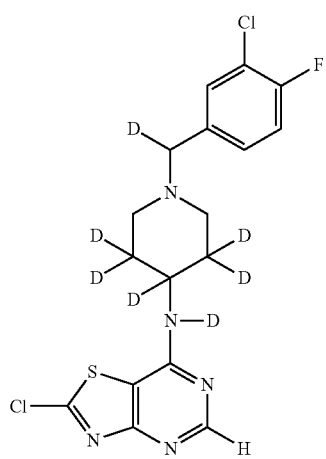

113

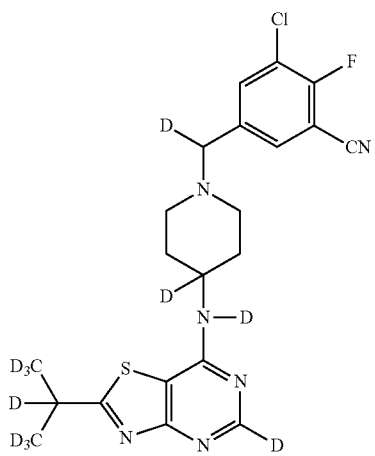

114

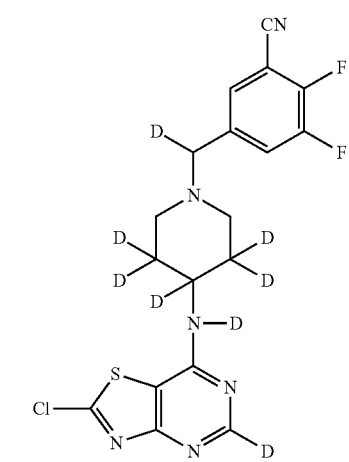

Equivalents

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages and modifications are within the scope of the invention. The contents of all references, issued patents and published patent applications cited in this application are hereby incorporated by reference. The appropriate components, processes, and methods of those patents, applications and other documents may be selected for the invention and embodiments thereof.

What is claimed is:

1. A method of treating liver cirrhosis, liver fibrosis, hepatocellular carcinoma, carcinoid syndrome, neuroendocrine neoplasia tumor progression, neuroendocrine neoplasia tumor fibrosis and neuroendocrine neoplasia tumor metastasis, comprising administering a pharmaceutically effective dose of a deuterium-enriched compound of formula I and the enantiomers, diastereomers, solvates and pharmaceutically acceptable salts thereof to a patient in need of such treatment,

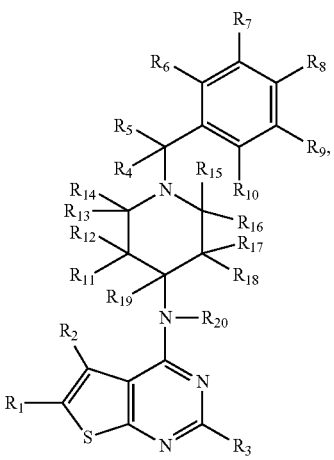

I wherein $R_1$ is D (Deuterium), F, Cl, $CD_3$, CN, $CF_3$, $CD(CD_3)_2$, i-Bu($d_{1-9}$), $O(CD_2CD_2CD_3)$, Phenyl-d5, 4-F-Ph-$d_4$, deuterated-thiophenyl-$d_3$, deuterated furanyl-$d_3$, deuterated thiazolyl-$d_3$, deuterated-pyridyl ($C_5D_4$), deuterated-imidazolyl -$d_3$ or deuterated-pyrrolyl-$d_4$;

$R_2$ is D, F, Cl, $CD_3$, $CF_3$, CN, $OCF_3$, $OCD_3$, $CD(CD_3)_2$, $C_6D_5$, 4-F—$C_6D_4$, 3-F—$C6D_4$, 2-F—$C_6D_4$; deuterated-thiophenyl-$d_3$, deuterated furanyl-$d_3$, deuterated thiazolyl -$d_3$, deuterated-pyridyl ($C_5D_4$), deuterated-imidazolyl-$d_3$ and deuterated-pyrrolyl-$d_4$;

$R_3$ is H, D, $CD_3$, $NHCD_3$, $NHCD_2CD_3$, $NHCD_2CD_2CD_3$, $NHCD_2CD_2CD_2CD_3$, $NHCD_2CD_2CD_2CD_2CD_3$; CN, F, Cl, $OCD_3$, $C_6D_5$ or pyridyl-$d_4$;

$R_4$ and $R_5$ independently are D or H, $CD_3$ or $CH_3$;

$R_6$, $R_7$, $R_8$, $R_9$ and $R_{10}$ independently are D, H, F, Cl, CN, $CD_3$, $CF_3$, $OCD_3$, $OCF_3$, $OCD_2CD_2CD_3$, $CONDCD_3$, $CON(CD_3)_2$ or $SO_2CD_3$;

$R_{11}$, $R_{12}$, $R_{13}$, $R_{14}$, $R_{15}$, $R_{16}$, $R_{17}$, $R_{18}$, and $R_{19}$ independently are D, F or H; and $R_{20}$ is D or H; and at least one of $R_2$, $R_5$, $R_9$, $R_{11}$, $R_{17}$, and $R_{18}$ is D.

2. A method of treating anxiety, depression, social phobia and panic disorder comprising administering a pharmaceutically effective dose of a deuterium-enriched compound of formula I, and the enantiomers, diastereomers, solvates and pharmaceutically acceptable salts thereof to a patient in need of such treatment,

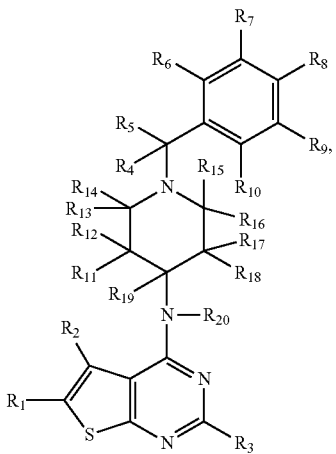

I wherein $R_1$ is D (Deuterium), F, Cl, $CD_3$, CN, $CF_3$, $CD(CD_3)_2$, i-Bu($d_{1-9}$), $O(CD_2CD_2CD_3)$, Phenyl-d5, 4-F—Ph-$d_4$, deuterated-thiophenyl -$d_3$, deuterated furanyl-$d_3$, deuterated thiazolyl-$d_3$, deuterated-pyridyl ($C_5D_4$), deuterated-imidazolyl -$d_3$ or deuterated-pyrrolyl-$d_4$;

$R_2$ is D, F, Cl, $CD_3$, $CF_3$, CN, $OCF_3$, $OCD_3$, $CD(CD_3)_2$, $C_6D_5$, 4-F—$C_6D_4$, 3-F—$C6D_4$, 2-F—$C_6D_4$; deuterated-thiophenyl-$d_3$, deuterated furanyl-$d_3$, deuterated thiazolyl -$d_3$, deuterated-pyridyl ($C_5D_4$), deuterated-imidazolyl-$d_3$ and deuterated-pyrrolyl-$d_4$;

$R_3$ is H, D, $CD_3$, $NHCD_3$, $NHCD_2CD_3$, $NHCD_2CD_2CD_3$, $NHCD_2CD_2CD_2CD_3$, $NHCD_2CD_2CD_2CD_2CD_3$; CN, F, Cl, $OCD_3$, $C_6D_5$ or pyridyl-$d_4$;

$R_4$ and $R_5$ independently are D or H, $CD_3$ or $CH_3$;

$R_6$, $R_7$, $R_8$, $R_9$ and $R_{10}$ independently are D, H, F, Cl, CN, $CD_3$, $CF_3$, $OCD_3$, $OCF_3$, $OCD_2CD_2CD_3$, $CONDCD_3$, $CON(CD_3)_2$ or $SO_2CD_3$;

$R_{11}$, $R_{12}$, $R_{13}$, $R_{14}$, $R_{15}$, $R_{16}$, $R_{17}$, $R_{18}$, and $R_{19}$ independently are D, F or H; and $R_{20}$ is D or H; and at least one of $R_2$, $R_5$, $R_9$, $R_{11}$, $R_{17}$, and $R_{18}$ is D.

3. The method of claim 1, wherein the deuterium enriched compound of formula I is, wherein $R_1$ is D, F, Cl or $CD(CD_3)_2$;
$R_2$ is D, F, CI, $CD_3$, $CF_3$ or CN;
$R_3$ is H or D;
$R_4$ and $R_5$ are D, H or $CD_3$;
$R_6$, $R_7$, $R_8$, $R_9$ and $R_{10}$ independently are D, H, F, Cl, CN or $CF_3$;
$R_{11}$, $R_{12}$, $R_{13}$, $R_{14}$, $R_{15}$, $R_{16}$, $R_{17}$, $R_{18}$, and $R_{19}$ are D or H; and
R20 is H or D;

and the abundance of deuterium is at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 81%, 83%, 84%, 85%, 86%, 87%, 88%, 89%, 90%, 91%, 92%, 93%, 94%, 95%, 96%, 97%, 98%, 99% and 100%.

4. The method of claim 1, wherein the compound is selected from the compounds of claim 1, wherein $R_1$ is D, Cl or $CD(CD_3)_2$;
$R_2$ is D, F, Cl or $CD(CD_3)_2$;
$R_3$ is H or D;
$R_4$ and $R_5$ are D, H;
$R_6$, $R_7$, $R_8$, $R_9$ and $R_{10}$ are D, H, F, Cl or CN;
$R_{11}$, $R_{12}$, $R_{17}$, $R_{18}$, and $R_{19}$ are D; and
R20 is D;

and the abundance of deuterium is at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 545, 55%, 56%, 57%, 58%, 59%, 60%, 61%, 62%, 63%, 64%, 65%, 66%, 43 67%, 68%, 69%, 70%, 71%, 72%, 73%, 74%, 75%, 76%, 77%, 78%, 79%, 80%, 81%, 81%, 83%, 84%, 85%, 86%, 87%, 88%, 89%, 90%, 91%, 92%, 93%, 94%, 95%, 96%, 97%, 98%, 99% and 100%.

5. The method of claim 1, wherein the compound is selected from the compounds of claim 1, wherein $R_1$ is D, Cl, or $CD(CD_3)_2$;
$R_2$ is D, F or Cl;
$R_3$ is H, D;
$R_4$ and $R_5$ are D or H;
$R_6$ is H, or D;
$R_7$ is D, F, Cl, or CN;
$R_8$ is D or F;
$R_9$ is D, F, Cl or CN;
$R_{10}$ is D, H or F;
$R_{11}$, $R_{12}$, $R_{17}$, $R_{18}$, and $R_{19}$ are D; and
$R_{20}$ is D;

and the abundance of deuterium is at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%,47%, 48%, 49%, 50%, 51%, 52%, 53%, 545, 44 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 81%, 83%, 84%, 85%, 86%, 87%, 88%, 89%, 90%, 91%, 92%, 93%, 94%, 95%, 96%, 97%, 98%, 99% and 100%.

6. The method of claim 1, wherein the compound is selected from the compounds of claim 1, when $R_1$ is Cl or $CD(CD_3)_2$;
$R_2$ is D;
$R_3$ is D;
$R_4$ is D;
$R_5$ is D;
$R_6$ is H;
$R_7$ is F or CN;
$R_8$ is F;
$R_9$ is D, F or CN;
$R_{10}$ is H;
$R_{11}$, $R_{12}$, $R_{17}$, $R_{18}$, and $R_{19}$ are D;
$R_{20}$ is D.

7. The method of claim 1, wherein the compound is selected from the compounds of claim 1, wherein $R_1$ is Cl, $CD(CD_3)_2$;
$R_2$ is D;
$R_3$ is D;
$R_4$ is D;
$R_5$ is D;

R$_6$ is H;
R$_7$ is F or CN;
R$_8$ is F;
R$_9$ is D;
R$_{10}$ is H;
R$_{11}$, R$_{12}$, R$_{17}$, R$_{18}$, and R$_{19}$ are D;
R$_{20}$ is D.

8. The method of claim 1, wherein the compound is selected from the compounds of claim 1, wherein
R$_1$ is Cl, CD(CD$_3$)$_2$;
R$_2$ is D;
R$_3$ is D;
R$_4$ is D;
R$_5$ is D;
R$_6$ is H;
R$_7$ is CN;
R$_8$ is F;
R$_9$ is D;
R$_{10}$ is H;
R$_{11}$, R$_{12}$, R$_{17}$, R$_{18}$, and R$_{19}$ are D; and
R$_{20}$ is D.

9. The method of claim 1, wherein the compound is selected from the compounds of claim 1, wherein
R$_1$ is Cl;
R$_2$ is D;
R$_3$ is D;
R$_4$ is D;
R$_5$ is D;
R$_6$ is H;
R$_7$ is CN;
R$_8$ is F;
R$_9$ is D;
R$_{10}$ is H;
R$_{11}$, R$_{12}$, R$_{13}$, R$_{14}$, R$_{15}$, R$_{16}$, R$_{17}$, R$_{18}$, and R$_{19}$ are H; and
R$_{20}$ is D.

10. The method of claim 1 wherein the deuterium-enriched compound is selected from the group consisting of:

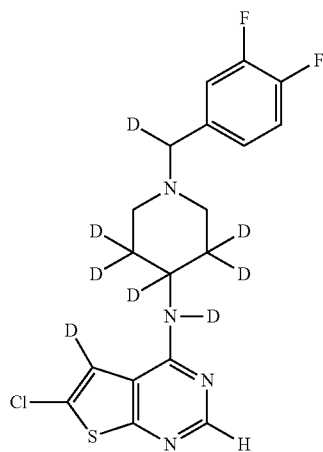

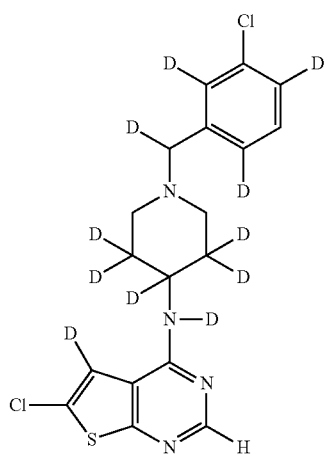

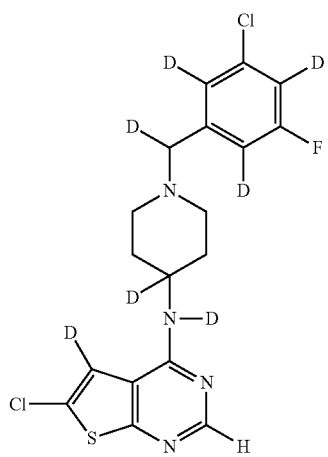

-continued
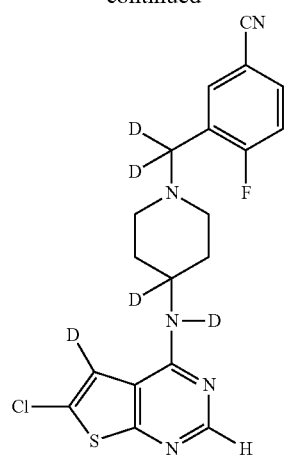
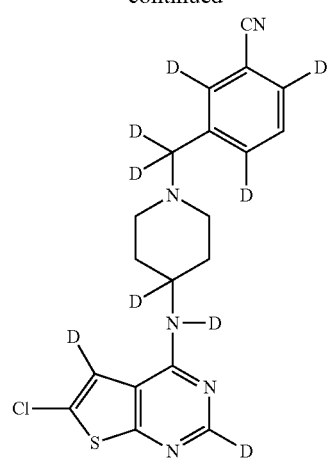
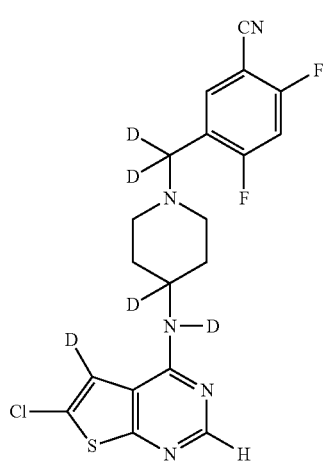
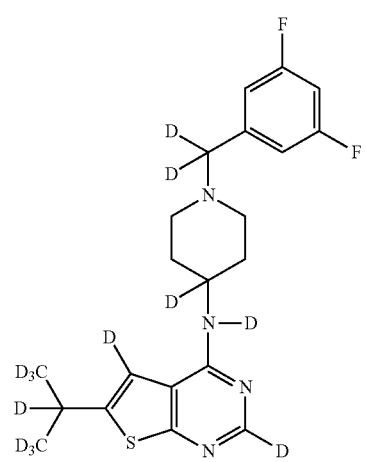
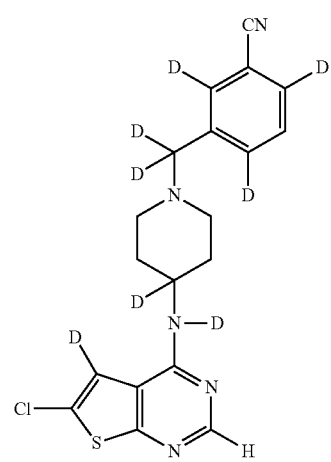
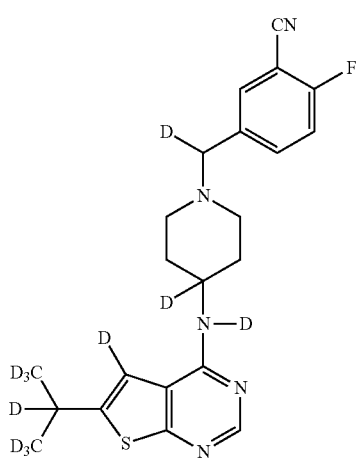

85
-continued
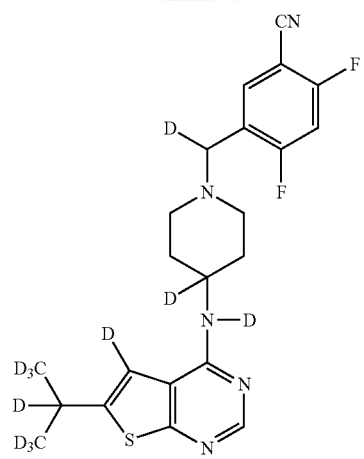
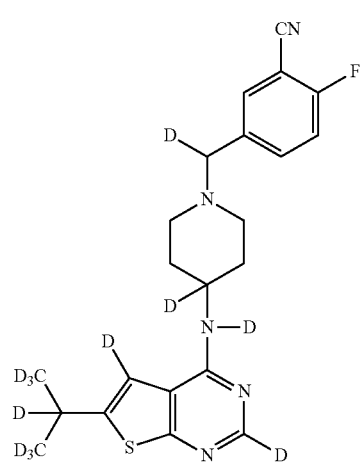
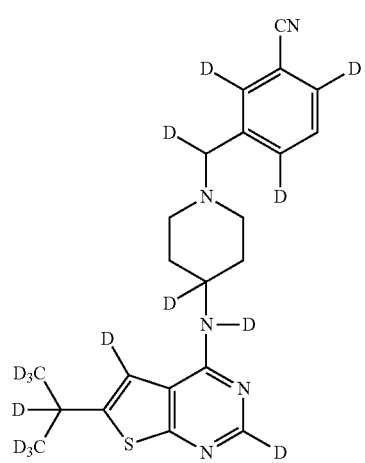
86
-continued
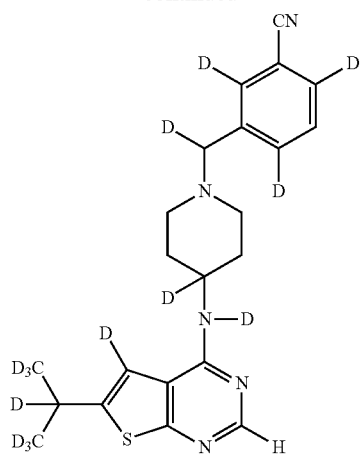
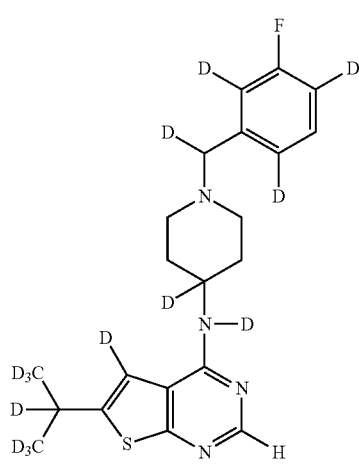
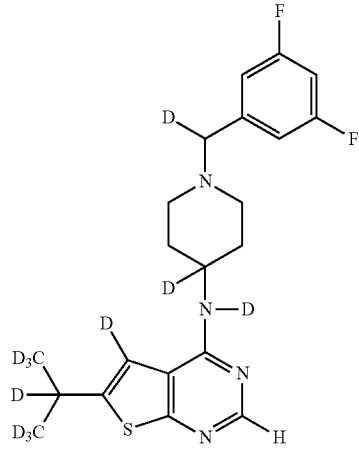

87
-continued
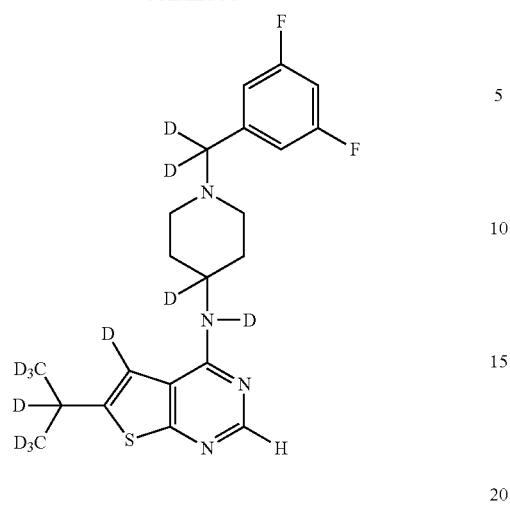
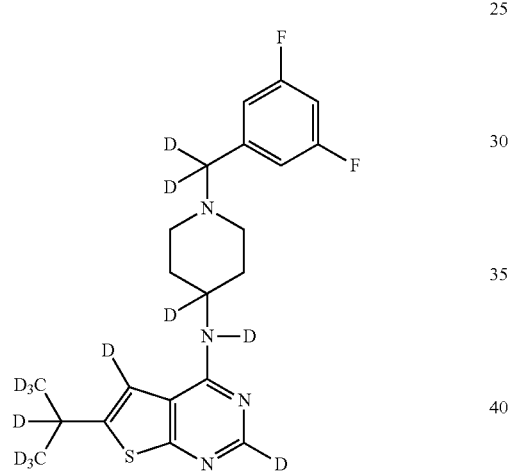
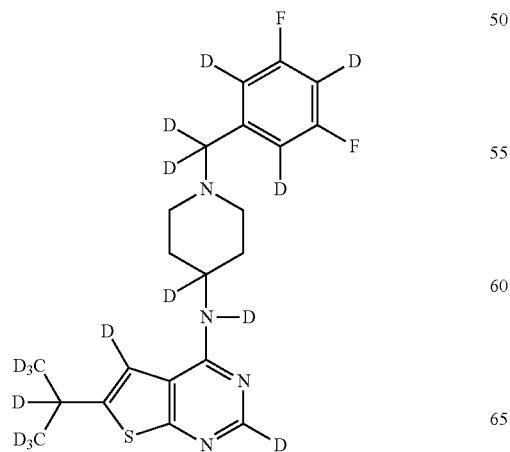
88
-continued
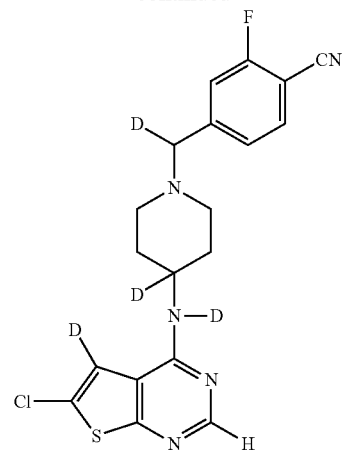
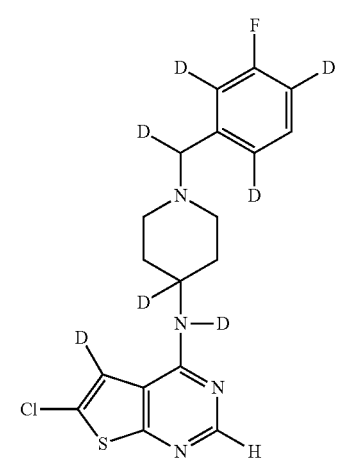
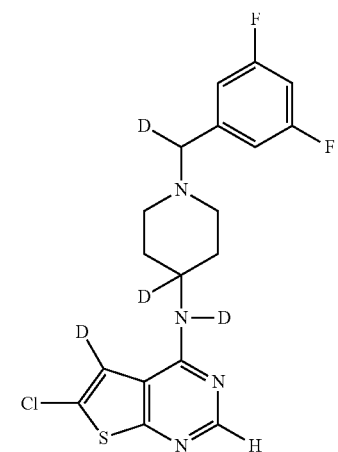

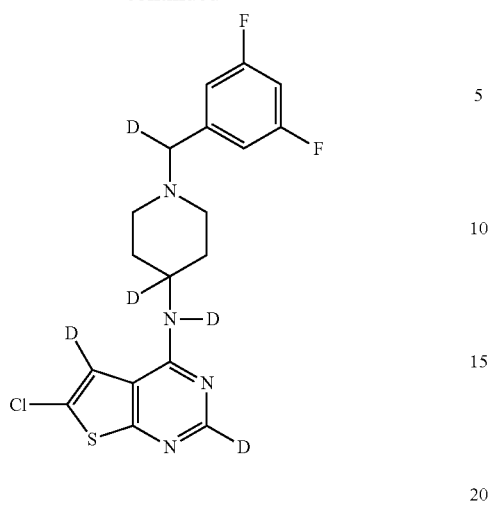
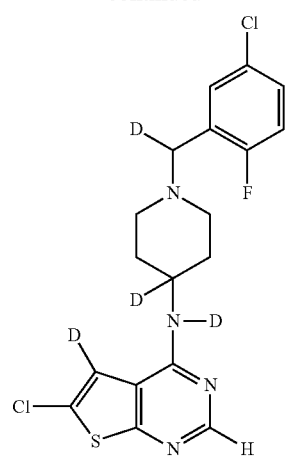
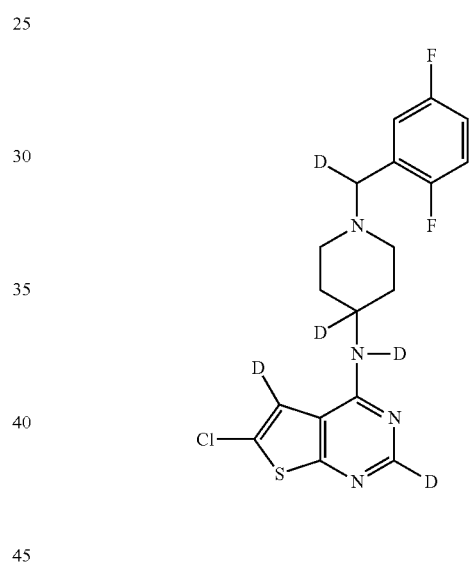
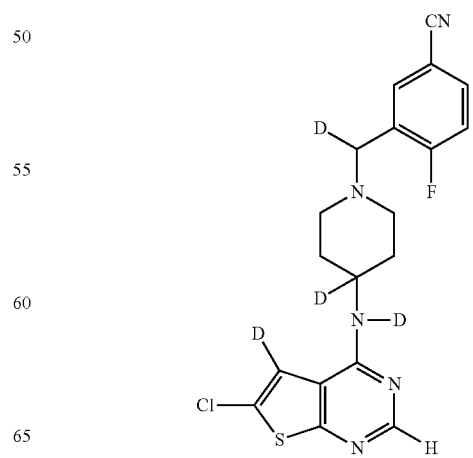

91

93
-continued
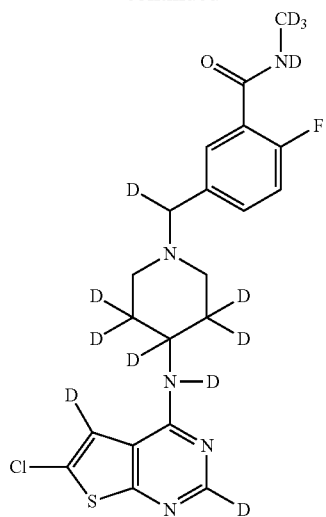
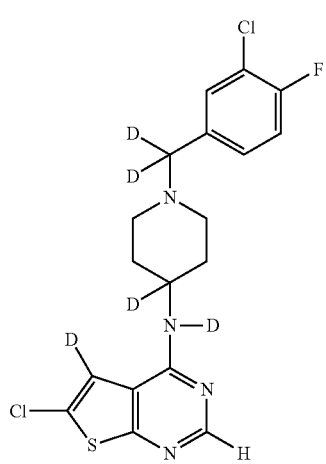
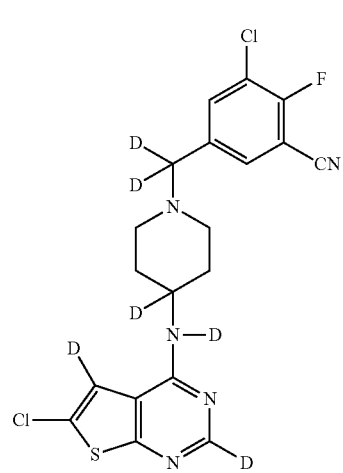
94
-continued
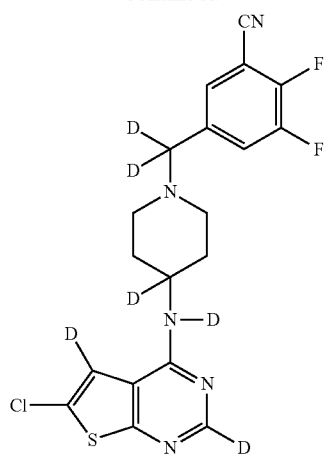
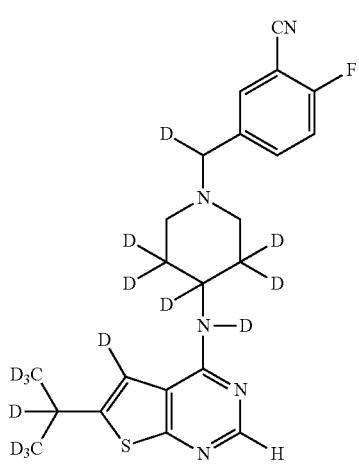
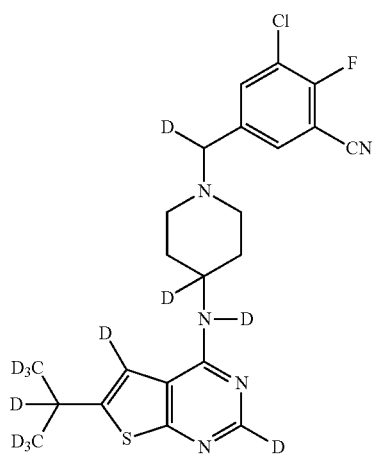

-continued

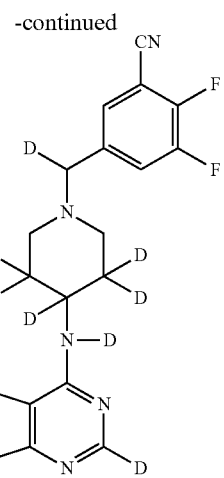

and pharmaceutically acceptable salts thereof.

11. The deuterium enriched compound of claim 1, wherein the pharmaceutically acceptable salts are selected from the group consisting of salts of the acids, HCl, HBr, HI, acetic, trifluoroacetic, citric, maleic, fumaric, tartaric, ascorbic, benzoin, methanesulfonic, benzenesulfonic, bicarbonic, carbonic, ethane disulfonic, edetic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenyllacetic, phosphoric, polygalacturonic, propionic, salicyclic, stearic, subacetic, succinic, sulfamic, sulfanilic, sulfuric, tannic, tartaric, tolouenesulfonic, and p-bromobenzenesulfonic.

12. The deuterium enriched compounds of claim 11, wherein the pharmaceutically acceptable salt is maleate, fumarate, HCl, oxalate, citrate or tartrate.

13. The method of claim 1, wherein, the pharmaceutically effective compound of formula I, is used in combination with a compound selected from the group consisting of Somfenib, Regorafenib, Imitanib and Erlotinib Sunitinib, Nilotinib, Dasatinib, Bosutinib, Ponatinib, Bafetinib, and Paclitaxel.

14. A method of treating pulmonary arterial hypertension, pulmonary hypertension associated with chronic obstructive pulmonary disease (COPD), right ventricular hypertrophy, pulmonary vascular remodeling, heart failure, and asthma comprising, administering a deuterium-enriched compound of formula I to a patient in need thereof,

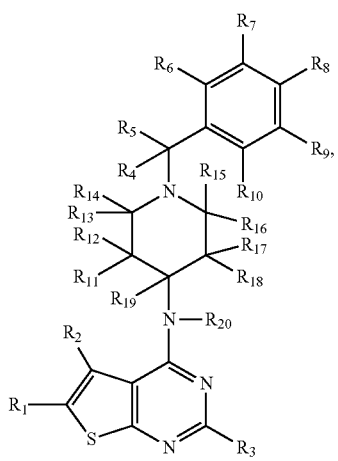

wherein $R_1$ is D (Deuterium), F, Cl, $CD_3$, CN, $CF_3$, $CD(CD_3)_2$, i-Bu($d_{1-9}$), $O(CD_2CD_2CD_3)$, Phenyl-d5, 4-F-Ph-$d_4$, deuterated-thiophenyl -$d_3$, deuterated furanyl-$d_3$, deuterated-pyridyl ($C_5D_4$), deuterated-imidazolyl-$d_3$, or deuterated-pyrrolyl-$d_4$;

$R_2$ is D, F, Cl, $CD_3$, $CF_3$, CN, $OCF_3$, $OCD_3$, $CD(CD_3)_2$, $C_6D_5$, 4-F—$C_6D_4$, 3-F—$C6D_4$, 2-F—$C_6D_4$, deuterated-imidazolyl-$d_3$ and deuterated -pyrrolyl-$d_4$;

$R_3$ is H, D, $CD_3$, $NHCD_3$, $NHCD_2CD_3$, $NHCD_2CD_2CD_3$, $NHCD_2CD_2CD_2CD_3$, $NHCD_2CD_2CD_2CD_2CD_3$; CN, F, Cl, $OCD_3$, $C_6D_5$, pyridyl-$d_4$, $R_4$ and $R_5$ independently are D or H, $CD_3$, $CH_3$;

$R_6$, $R_7$, $R_8$, $R_9$ and $R_{10}$ independently are D, H, F, Cl, CN, $CD_3$, $CF_3$, $OCD_3$, $OCF_3$, $OCD_2CD_2CD_3$, $CONDCD_3$, $CON(CD_3)_2$, $SO_2CD_3$;

$R_{11}$, $R_{12}$, $R_{13}$, $R_{14}$, $R_{15}$, $R_{16}$, $R_{17}$, $R_{18}$, and $R_{19}$ independently are D, F, H; and $R_{20}$ is D or H; and at least one of $R_2$, $R_5$, $R_9$, $R_{11}$, $R_{17}$, and $R_{18}$ is D, in combination with a therapeutic agent selected from the group consisting of bosentan, ambrisentan, sitaxentan, macitentan, sildenafil, tadalafil, vardenafil, epoprostenol, iloprost, losartan, valsartan, irbesartan, candesartan, and/or aliskiren.

15. The method of claim 14, wherein the deuterium enriched compounds of formula I is, wherein $R_1$ is D, F, Cl or $CD(CD_3)_2$;

$R_2$ is D, F, Cl, $CD_3$, $CF_3$ or CN;

$R_3$ is H, or D;

$R_4$ and $R_5$ are D, H or $CD_3$;

$R_6$, $R_7$, $R_8$, $R_9$ and $R_{10}$ independently are D, H, F, Cl, CN or $CF_3$;

$R_{11}$, $R_{12}$, $R_{13}$, $R_{14}$, $R_{15}$, $R_{16}$, $R_{17}$, $R_{18}$, and $R_{19}$ are D, or H; and R20 is H or D;

and the abundance of deuterium is at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 81%, 83%, 84%, 85%, 86%, 87%, 88%, 89%, 90%, 91%, 92%, 93%, 94%, 95%, 96%, 97%, 98%, 99% and 100%.

16. The method of claim 1, wherein the diseases being treated are liver fibrosis, and liver cirrhosis.

17. The method of claim 1, wherein the diseases being treated are hepatocellular carcinoma, carcinoid syndrome, neuroendocrine neoplasia tumor progression, neuroendocrine neoplasia tumor fibrosis and neuroendocrine neoplasia tumor.

18. The method of claim 2, wherein the diseases being treated are anxiety and depression.

19. The method of claim 14, wherein the diseases being treated are pulmonary arterial hypertension (PAH), pulmonary hypertension associated with chronic obstructive pulmonary disease (COPD).

* * * * *